United States Patent
Yerramilli

(10) Patent No.: US 8,361,496 B2
(45) Date of Patent: *Jan. 29, 2013

(54) PHOSPHOLIPID GEL COMPOSITIONS FOR DRUG DELIVERY AND METHODS OF TREATING CONDITIONS USING SAME

(75) Inventor: Murthy V. S. N. Yerramilli, Falmouth, ME (US)

(73) Assignee: Idexx Laboratories Inc., Westbrook, ME (US)

( * ) Notice: Subject to any disclaimer, the term of this patent is extended or adjusted under 35 U.S.C. 154(b) by 199 days.

This patent is subject to a terminal disclaimer.

(21) Appl. No.: 12/908,993

(22) Filed: Oct. 21, 2010

(65) Prior Publication Data

US 2011/0034430 A1    Feb. 10, 2011

Related U.S. Application Data

(63) Continuation of application No. 11/159,203, filed on Jun. 23, 2005, now Pat. No. 7,846,472, which is a continuation-in-part of application No. 11/019,218, filed on Dec. 23, 2004, now Pat. No. 7,858,115, which is a continuation-in-part of application No. 10/874,532, filed on Jun. 24, 2004, now Pat. No. 7,854,943.

(51) Int. Cl.
*A61K 9/27* (2006.01)

(52) U.S. Cl. ....................................... 424/450
(58) Field of Classification Search .................. 424/450; 514/178

See application file for complete search history.

(56) References Cited

U.S. PATENT DOCUMENTS

| | | |
|---|---|---|
| 2,909,466 A | 10/1959 | Neumann et al. |
| 4,025,620 A | 5/1977 | Beyer et al. |
| 4,141,981 A | 2/1979 | Draber et al. |
| 4,678,516 A | 7/1987 | Alderman et al. |
| 4,814,173 A | 3/1989 | Song et al. |
| 4,837,008 A | 6/1989 | Rudy et al. |
| 4,837,213 A | 6/1989 | Caron et al. |
| 4,843,096 A | 6/1989 | Stiefel |
| 4,847,267 A | 7/1989 | Deckner et al. |
| 5,110,809 A | 5/1992 | Wang et al. |
| 5,446,070 A | 8/1995 | Mantelle |
| 5,480,649 A | 1/1996 | Akazawa et al. |
| 5,516,808 A | 5/1996 | Sawaya |
| 5,641,890 A | 6/1997 | Wesley et al. |
| 5,665,365 A | 9/1997 | Bombardelli et al. |
| 5,681,849 A | 10/1997 | Richter et al. |
| 5,695,784 A | 12/1997 | Pollinger et al. |
| 5,736,152 A | 4/1998 | Dunn |
| 5,856,355 A | 1/1999 | Richter et al. |
| 5,863,549 A | 1/1999 | Tarantino |
| 5,886,041 A | 3/1999 | Yu et al. |
| 5,985,259 A | 11/1999 | Cagle et al. |
| 5,994,372 A | 11/1999 | Yaksh |
| 6,005,001 A | 12/1999 | Richter et al. |
| 6,018,033 A | 1/2000 | Chen et al. |
| 6,080,744 A | 6/2000 | Ayon-Covarrubias |
| 6,117,864 A | 9/2000 | Morita et al. |
| 6,121,314 A | 9/2000 | Richter et al. |
| 6,130,200 A | 10/2000 | Brodbeck et al. |
| 6,146,664 A | 11/2000 | Siddiqui |
| 6,165,987 A | 12/2000 | Harvey |
| 6,214,339 B1 | 4/2001 | Pellico |
| 6,238,683 B1 | 5/2001 | Burnett et al. |
| 6,436,455 B2 | 8/2002 | Zietlow et al. |
| 6,464,987 B1 | 10/2002 | Fanara et al. |
| 6,565,873 B1 | 5/2003 | Shefer et al. |
| 6,645,528 B1 | 11/2003 | Straub et al. |
| 6,669,958 B1 | 12/2003 | Trager et al. |
| 6,787,568 B1 | 9/2004 | Mihalik |
| 7,220,431 B2 | 5/2007 | Sawchuk et al. |
| 7,846,472 B2 * | 12/2010 | Murthy .................. 424/450 |
| 7,854,943 B2 * | 12/2010 | Murthy .................. 424/450 |
| 7,858,115 B2 * | 12/2010 | Murthy .................. 424/450 |
| 2002/0142050 A1 | 10/2002 | Straub et al. |
| 2004/0057991 A1 | 3/2004 | Hui et al. |
| 2004/0138179 A1 | 7/2004 | Goldstein et al. |
| 2004/0197408 A1 | 10/2004 | Gravett |
| 2004/0204471 A1 * | 10/2004 | Seibert .................. 514/406 |
| 2004/0214753 A1 | 10/2004 | Britten et al. |
| 2004/0220264 A1 | 11/2004 | Yu et al. |
| 2004/0235803 A1 | 11/2004 | Britten et al. |
| 2005/0009931 A1 | 1/2005 | Britten et al. |
| 2005/0239722 A1 | 10/2005 | Albert et al. |
| 2005/0287220 A1 | 12/2005 | Murthy |
| 2006/0073198 A1 | 4/2006 | Boni et al. |

FOREIGN PATENT DOCUMENTS

| | | |
|---|---|---|
| CA | 2111773 | 6/1994 |
| CA | 2381571 | 3/2001 |
| CH | 1383816 | 12/2002 |
| EP | 0081896 | 6/1983 |
| EP | 0694305 | 1/1996 |
| JP | 60087215 | 5/1985 |
| JP | 10-194994 | 7/1998 |
| WO | WO 98/36776 | 8/1998 |
| WO | WO 99/30690 | 6/1999 |
| WO | WO 00/09117 | 2/2000 |
| WO | WO 01/01959 | 1/2001 |
| WO | WO 03/034988 | 1/2003 |

OTHER PUBLICATIONS

Supplementary European Search Report, Mailed Apr. 12, 2012.
Handbook of Pharmaceutical Controlled Release Technology (ed. Wise) 2000, Chapters 1, 3 and 22.
Shang-Jin He et al., Chinese Journal of Applied Chemistry, (Aug. 2002) vol. 19(8), pp. 742-745 (abstract).

*Primary Examiner* — Blessing Fubara
(74) *Attorney, Agent, or Firm* — Haynes and Boone, LLP

(57) ABSTRACT

The present invention relates to pharmaceutical compositions in the form of a gel for controlled- or sustained-release of a pharmaceutically active agent and to methods for treating or preventing a condition in an animal by administering to an animal in need thereof the pharmaceutical compositions. One particular type of condition for which the pharmaceutical compositions are useful is a microbial infection, e.g., of the skin, ear, or eye, especially for veterinary applications.

23 Claims, No Drawings

PHOSPHOLIPID GEL COMPOSITIONS FOR DRUG DELIVERY AND METHODS OF TREATING CONDITIONS USING SAME

1. CROSS-REFERENCE TO RELATED APPLICATIONS

This application is a continuation of application Ser. No. 11/159,203 filed on Jun. 23, 2005, which is a continuation-in-part of application Ser. No. 11/019,218 filed 23 Dec. 2004, which is a continuation-in-part of application Ser. No. 10/874,532 filed 24 Jun. 2004, the contents of which are incorporated herein by reference.

2. STATEMENT REGARDING FEDERALLY SPONSORED RESEARCH OR DEVELOPMENT

Not Applicable.

3. INCORPORATION-BY-REFERENCE OF MATERIAL SUBMITTED ON A COMPACT DISC

Not Applicable.

4. BACKGROUND OF THE INVENTION

4.1 Field of the Invention

The present invention relates to pharmaceutical compositions in the form of a gel for controlled- or sustained-release of a pharmaceutically active agent and to methods for treating or preventing a condition in an animal by administering to an animal in need thereof the pharmaceutical compositions. The pharmaceutical compositions are suitable for oral, topical, otic, and ophthalmic applications. One particular type of condition for which the pharmaceutical compositions are useful is a microbial infection, e.g., of the skin, ear, or eye, especially for veterinary applications.

4.2 Description of Related Art

It is often desirable to administer drugs using controlled- or sustained-release formulations that can maintain at least a minimum therapeutic level, for example, a blood level, of the drug over extended periods of time. These controlled- or sustained-release formulations reduce the frequency of dosing, for enhanced convenience and compliance, and also reduce the severity and frequency of side effects. For example, by maintaining substantially constant blood levels and avoiding blood level fluctuations of the drug, such as are associated with conventional immediate release formulations that are administered several times a day, controlled- or sustained-release formulations can provide a better therapeutic profile than is obtainable with conventional immediate release formulations.

Known methods for controlled- or sustained-drug release include implanted devices, such as osmotic pumps, and drug dispersed in a biocompatible polymer matrix, which can be implanted, administered orally, or injected. Examples of biocompatible polymers used in such applications include poly(lactic acid) and poly(lactic acid-co-glycolic acid). The polymer typically undergoes slow hydrolysis in vivo to continually release the entrapped drug over time. The polymer degradation products are non-toxic and absorbed or metabolized by the body. For example, when the biocompatible polymer is poly(lactic acid) or poly(lactic acid-co-glycolic acid), the degradation products are the parent acids, lactic acid and glycolic acid, which are absorbed by the body.

U.S. Pat. No. 5,110,809 to Wang et al. discloses a stable anhydrous gel formulations for topical antifungal use containing an imidazole, a steroid, a co-solvent system comprising monohydric and dihydric alcohols, and a hydroxyalkylcellulose gellant.

International Publication No. WO 00/09117 discloses topical pharmaceutical compositions containing nimesulfide, a non-steroidal anti-inflammatory agent having poor solubility in water.

U.S. Pat. No. 6,214,339 to Pellico discloses a treatment for otitis externa in cats and dogs that comprises administering a substantially non-aqueous, di-enzymatic therapeutic composition, in a liquid or gel fluid carrier. An illustrative composition contains glucose, glucose oxidase, potassium iodide, and lactoperoxidase in a fluid mixture of glycerol and propylene glycol.

Eurasian Patent No. EA 0002978 B1 claims in the primary independent claim a process for preparing a phospholipid suspension.

U.S. patent application no. US 2004/0220264 discloses compositions, methods of making the compositions, and uses of compositions that include a molecular complex between an acidic pharmaceutical drug and a functional substance. The functional substance can be an alkaline amino acid, an amino acid amide, an amino acid ester, or a related amino acid. The compositions are allegedly useful for delivering the drug into cutaneous tissue.

U.S. patent application no. US 2004/0197408 discloses formulations of a diblock copolymer having a hydrophobic block and hydrophilic block, an additive selected from an amino acid, and an oligopeptide. The formulations, when admixed with water, form drug delivery vehicles in micellar form.

There remains a need in the art, however, for drug-containing pharmaceutical compositions, especially drug-containing pharmaceutical compositions suitable for oral, topical, otic, and ophthalmic applications, that provide controlled- and/or sustained-release of the drug contained therein.

Citation of any reference in Section 1 of this application is not to be construed that such reference is prior art to the present application.

5. SUMMARY OF THE INVENTION

These and other features and advantages of the present invention will become apparent from the remainder of the disclosure, in particular the following detailed description of the preferred embodiments, all of which illustrate by way of example the principles of the invention.

The invention relates to pharmaceutical compositions that provide sustained- or controlled-release of a pharmaceutically active compound.

In one embodiment, the pharmaceutical compositions comprise (i) a phospholipid or sphingomyelin; (ii) a polar aprotic organic solvent; (iii) a polar protic organic solvent; and (iv) a pharmaceutically active agent, wherein the pharmaceutical composition is in the form of a gel.

In one embodiment, the pharmaceutical compositions comprise (i) a phospholipid or sphingomyelin, (ii) a solvent of selected from the group consisting of propylene glycol substantially free of other organic solvents and glycerol formal substantially free of other organic solvents, and (iii) a pharmaceutically active agent, wherein the pharmaceutical composition is in the form of a gel. In one embodiment, the solvent is glycerol formal substantially free of other organic solvents. In one embodiment, the solvent is propylene glycol substantially free of other organic solvents.

The invention further relates to a method of treating a condition in an animal comprising administering to an animal in need thereof a pharmaceutical composition of the invention.

6. BRIEF DESCRIPTION OF THE DRAWINGS

Not Applicable.

7. DETAILED DESCRIPTION OF THE INVENTION

The invention relates to pharmaceutical compositions for controlled- or sustained-release of a pharmaceutically active agent. In one embodiment, the pharmaceutical compositions comprise (i) a phospholipid or spingomyelin, (ii) a first organic solvent, (iii) a second organic solvent, and (iv) a therapeutically effective amount of a pharmaceutically active agent in relative amounts sufficient to cause formation of a gel.

In another embodiment, the pharmaceutical compositions comprise (i) a phospholipid or sphingomyelin, a solvent of selected from the group consisting of propylene glycol substantially free of other organic solvents and glycerol formal substantially free of other organic solvents, and (iii) a therapeutically effective amount of a pharmaceutically active agent in relative amounts sufficient to cause formation of a gel.

The invention further relates a method of treating or preventing a condition in an animal. The method comprises administering to an animal in need thereof a therapeutically effective amount of a pharmaceutically active agent by orally, topically, otically, and/or ophthalmically administering a pharmaceutical composition of the invention.

7.1 Definitions

As used herein, the term "gel" means a material having an average viscosity of at least about 1,000 centipoise ("cP"), preferably at least about 2,000 cP, more preferably at least about 5,000 cP, even more preferably at least about 7,500 cP, and most preferably at least about 10,000 cP but less than about 100,000 cP, preferably less than about 75,000 cP at 20° C. Typically, a gel exhibits quiescent and/or dynamic interaction between its components, e.g., in the form of association complexes, which are generally reversible by application of force (e.g., shear) and/or temperature to achieve flow.

As used herein, the term "phospholipid" means a compound having the general formula:

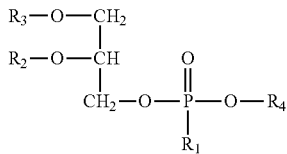

wherein
$R_1$ is —OH or —O$^-$;
$R_2$ is:
(i) —H, or
(ii) a $C_2$-$C_{36}$ saturated or unsaturated, linear or branched acyl group;

$R_3$ is:
(i) —H,
(ii) a $C_2$-$C_{36}$ saturated or unsaturated, linear or branched acyl group; or
(iii) —C=C—$R_9$ wherein $R_9$ is a $C_1$-$C_{22}$ saturated or unsaturated, linear or branched hydrocarbon group, optionally substituted with one or more nitrogen containing groups;
and at least one of $R_2$ or $R_3$ is not —H;
$R_4$ is:
(i) —H;
(i) —(CH$_2$)$_n$—$R_5$,
wherein $R_5$ is —N($R_6$)($R_7$) or —N$^+$($R_6$)($R_7$)($R_8$),
$R_6$, $R_7$, and $R_8$ are each independently —H, $C_1$-$C_3$ alkyl group, or $R_6$ and $R_7$ are connected to form a 5- or 6-membered heterocyclic ring with the nitrogen, and
n is an integer ranging from 1 to 4, preferably 2;

(iii)
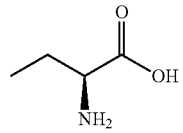

(iv)
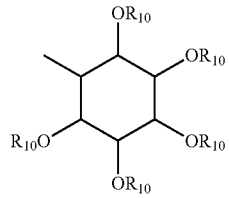

wherein each $R_{10}$ is independently —H or —P(O)(OH)$_2$; or
(v) —CH$_2$CH(OH)CH$_2$(OH).

As used herein, the term "saturated or unsaturated, linear or branched $C_2$-$C_{36}$ acyl group" means a group of formula —O—C(O)—R, wherein R is a $C_1$-$C_{35}$ hydrocarbon group that can be saturated or unsaturated, linear or branched.

As used herein, the term "spingomyelin" means a compound having the general formula:

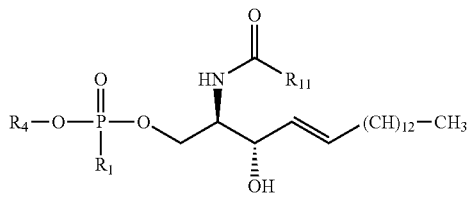

wherein
$R_1$ is —OH or —O$^-$;
$R_4$ is:
(i) —H; or
(i) —(CH$_2$)$_n$—$R_5$,
wherein $R_5$ is —N($R_6$)($R_7$) or —N$^1$($R_6$)($R_7$)($R_8$),
$R_6$, $R_7$, and $R_8$ are each independently —H, $C_1$-$C_3$ alkyl, or $R_6$ and $R_7$ are connected to form a 5- or 6-membered heterocyclic ring with the nitrogen, and n is an interger ranging from 1 to 4, preferably 2; and $R_{11}$ is a $C_1$-$C_{22}$ saturated or unsaturated, linear or branched hydrocarbon group optionally substituted with one or more nitrogen containing groups.

As used herein, the term "fatty acid" means a carboxylic acid of formula R—C(O)OH, wherein R is $C_6$-$C_{22}$ linear or branched, saturated or unsaturated, hydrocarbon group. Representative fatty acids include, but are not limited to, caproic acid, caprylic acid, capric acid, lauric acid, myristic acid, palmitic acid, stearic acid, palmic acid, palmitoleic acid, oleic acid, linoleic acid, and linolenic acid.

As used herein, the term "organic solvent" means any organic compound, or a mixture of organic compounds, that is a fluid at or above about 20° C., preferably at or above about 10° C., more preferably at or above about 0° C., most preferably at or above about −10° C. Typical organic solvents have a molecular weight of not more than about 500 g/mol and preferably not more than 100 g/mol. When organic solvents are administered to an animal, it is preferred that the organic solvents are compounds that do not significantly induce undue adverse effects such as excessive toxicity, irritation, or allergic response commensurate with a reasonable benefit/risk ratio (i.e., "pharmaceutically acceptable organic solvents").

As used herein, the term "polar aprotic organic solvent" means an organic solvent that has a dielectric constant greater than about 20, preferably greater than about 30, and more preferably greater than about 50, and does not include an OH functional group.

As used herein, the term "polar protic organic solvent" means an organic solvent that has a dielectric constant greater than about 20, preferably greater than about 30, and more preferably greater than about 50, and includes an —OH functional group.

As used herein, the term "pharmaceutically active agent" means a compound that causes a pharmacological effect in an animal. Typically, the pharmacological effect is treating or preventing a condition in an animal. A pharmaceutically active agent can advantageously include a drug in its biologically active form, a pro-drug in a form such that the biologically active drug form is created in vivo in the animal, a drug metabolite, or a pharmaceutically acceptable salt or ester of a biologically active drug.

The term "animal," as used herein, includes, but is not limited to, humans, canines, felines, equines, bovines, ovines, porcines, amphibians, reptiles, and avians. Representative animals include, but are not limited to a cow, a horse, a sheep, a pig, an ungulate, a chimpanzee, a monkey, a baboon, a chicken, a turkey, a mouse, a rabbit, a rat, a guinea pig, a dog, a cat, and a human. In one embodiment, the animal is a mammal. In one embodiment, the animal is a human. In one embodiment, the animal is a canine, a feline, an equine, a bovine, an ovine, or a porcine.

The term "condition," as used herein, means an interruption, cessation, or disorder of a bodily function, system, or organ, and includes diseases, defects, and disorders. Representative conditions include, but are not limited to, infections such as bacterial, viral, fungal, yeast, and parasitic infections; diseases such as cancer; inflammation; diabetes; and organ failure.

The terms "effective amount" and "therapeutically effective amount," as used herein, mean an amount sufficient for treating or preventing or preventing a condition in an animal.

The phrases "treating," "treatment of," and the like, include the amelioration or cessation of a specified condition.

The phrases "preventing," "prevention of," and the like, include the avoidance of the onset of a condition.

The phrase "pharmaceutically acceptable salt," as used herein, is a salt formed from an acid and a basic nitrogen group of a pharmaceutically active agent. Illustrative salts include, but are not limited, to sulfate; citrate; acetate; oxalate; chloride; bromide; iodide; nitrate; bisulfate; phosphate; acid phosphate; isonicotinate; lactate; salicylate; acid citrate; tartrate; oleate; tannate; pantothenate; bitartrate; ascorbate; succinate; maleate; gentisinate; fumarate; gluconate; glucaronate; saccharate; formate; benzoate; glutamate; methanesulfonate; ethanesulfonate; benzenesulfonate; p-toluenesulfonate; pamoate (i.e., 1,1'-methylene-bis-(2-hydroxy-3-naphthoate)); and salts of fatty acids such as caproate, laurate, myristate, palmitate, stearate, oleate, linoleate, and linolenate salts. The phrase "pharmaceutically acceptable salt" also refers to a salt prepared from a pharmaceutically active agent having an acidic functional group, such as a carboxylic acid functional group, and a pharmaceutically acceptable inorganic or organic base. Suitable bases include, but are not limited to, hydroxides of alkali metals such as sodium, potassium, and lithium; hydroxides of alkaline earth metal such as calcium and magnesium; hydroxides of other metals, such as aluminum and zinc; ammonia, and organic amines, such as unsubstituted or hydroxy-substituted mono-, di-, or trialkylamines; dicyclohexylamine; tributyl amine; pyridine; N-methyl,N-ethylamine; diethylamine; triethylamine; mono-, bis-, or tris-(2-hydroxy-lower alkyl amines), such as mono-, bis-, or tris-(2-hydroxyethyl)amine, 2-hydroxy-tert-butylamine, or tris-(hydroxymethyl)methylamine, N,N,-di-lower alkyl-N-(hydroxy lower alkyl)-amines, such as N,N,-dimethyl-N-(2-hydroxyethyl)amine, or tri-(2-hydroxyethyl)amine; N-methyl-D-glucamine; and amino acids such as arginine, lysine, and the like.

The phrase "substantially free of," as used herein, means less than about 5 percent by weight, preferably less than about 2 percent by weight, more preferably less than about 1 percent by weight, even more preferably less than about 0.5 percent by weight, and most preferably less than about 0.2 percent by weight. For example, the phrase "propylene glycol (or glycerol formal) substantially free of other organic solvents" means that the amount of other organic solvents in the propylene glycol (or glycerol formal) is less than about 5 percent by weight, preferably less than about 2 percent by weight, more preferably less than about 1 percent by weight, even more preferably less than about 0.5 percent by weight, and most preferably less than about 0.2 percent by weight of the combined amount of the propylene glycol (or glycerol formal) and the other organic solvents.

4.2 The Phospholipid

Any pharmaceutically acceptable phospholipid can be used in the pharmaceutical compositions of the invention.

Representative, pharmaceutically acceptable phospholipids include, but are not limited to:

phosphatidic acids of general formula:

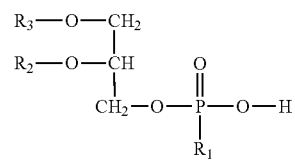

wherein $R_1$, $R_2$, and $R_3$ are defined above. Suitable phosphatidic acids suitable for use in the compositions and methods of the invention include, but are not limited to, the 1-acyl-2-acyl-sn-glycero-3-phosphates and the 1,2-diacyl-sn-glycero-3-phosphates commercially available from Avanti Polar Lipids Inc. of Alabaster, Ala.

phosphatidylethanolamines of general formula

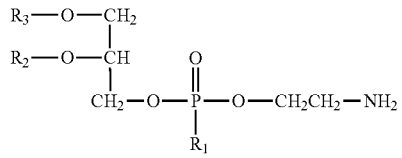

wherein $R_1$, $R_2$, and $R_3$ are defined above. Suitable phosphatidylethanolamines suitable for use in the compositions and methods of the invention include, but are not limited to, the 1-acyl-2-acyl-sn-glycero-3-phosphoethanolamines and the 1,2-diacyl-sn-glycero-3-phosphoethanolamines commercially available from Avanti Polar Lipids Inc. of Alabaster, Ala.

phosphatidylcholines of general formula

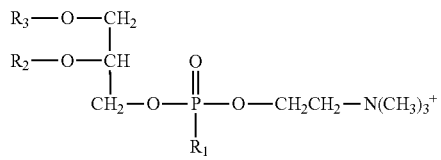

wherein $R_1$, $R_2$, and $R_3$ are defined above. Suitable phosphatidylcholines suitable for use in the compositions and methods of the invention include, but are not limited to, the 1-acyl-2-acyl-sn-glycero-3-phosphocholines, the 1,2-diacyl-sn-glycero-3-phosphoethanolamines (saturated series), and the 1,2-diacyl-sn-glycero-3-phosphoethanolamines (unsaturated series), commercially available from Avanti Polar Lipids Inc. of Alabaster, Ala. and Phospholipon®-50PG, Phospholipon®-53MCT, Phospholipon®-75SA, Phospholipon®-80, Phospholipon®-90NG, Phospholipon®-90H, and Phospholipon®-100H, commercially available from Phospholipid GmbH of Cologne, Germany. In one embodiment, the phospholipid is Phospholipon®-90H.

phosphatidylserines of general formula

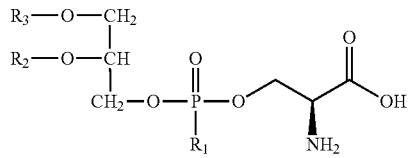

wherein $R_1$, $R_2$, and $R_3$ are defined above. Suitable phosphatidylserines suitable for use in the compositions and methods of the invention include, but are not limited to, the 1-acyl-2-acyl-sn-glycero-3-[phospho-L-serine]s and the 1,2-diacyl-sn-glycero-3-[phospho-L-serine]s commercially available from Avanti Polar Lipids Inc. of Alabaster, Ala.

plasmalogens of general formula

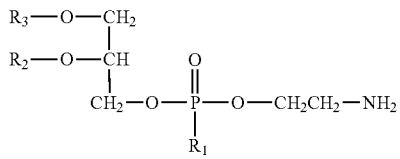

wherein $R_1$ and $R_2$ are defined above and $R_3$ is —C=C—$R_9$, wherein $R_9$ is defined above. Suitable plasmalogens suitable for use in the compositions and methods of the invention include, but are not limited to, C16(Plasm)-12:0 NBD PC, C16(Plasm)-18:1 PC, C16(Plasm)-20:4 PC, C16(Plasm)-22:6 PC, C16(Plasm)-18:1 PC, C16(Plasm)-20:4 PE, and C16(Plasm)-22:6 PE, commercially available from Avanti Polar Lipids Inc. of Alabaster, Ala.

phosphatidylglycerols of general formula

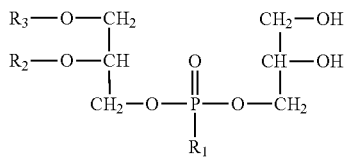

wherein $R_1$, $R_2$, and $R_3$ are defined above. Suitable phosphatidylglycerols suitable for use in the compositions and methods of the invention include, but are not limited to, the 1-acyl-2-acyl-sn-glycero-3-[phospho-rac-(1-glycerol)]s and the 1,2-diacyl-sn-glycero-3-[phospho-rac-(1-glycerol)]s, commercially available from Avanti Polar Lipids Inc. of Alabaster, Ala.

phosphatidylinositols of general formula

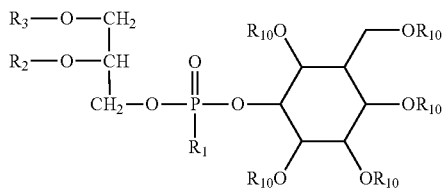

wherein $R_1$, $R_2$, $R_3$, and $R_{10}$ are defined above. Suitable phosphatidylinositols suitable for use in the compositions and methods of the invention include, but are not limited to, phosphatidylinositol, phosphatidylinositol-4-phosphate, and phosphatidylinositol-4,5-bisphosphate, commercially available from Avanti Polar Lipids Inc. of Alabaster, Ala.

The amount of phospholipid in the pharmaceutical composition typically ranges from about 0.1 percent to 10 percent by weight of the pharmaceutical composition.

In one embodiment, the amount of phospholipid in the pharmaceutical composition ranges from about 0.5 percent to 7 percent by weight of the pharmaceutical composition.

In one embodiment, the amount of phospholipid in the pharmaceutical composition ranges from about 1 percent to 4 percent by weight of the pharmaceutical composition.

In one embodiment, the amount of phospholipid in the pharmaceutical composition ranges from about 2 percent to 4 percent by weight of the pharmaceutical composition.

In one embodiment, the amount of phospholipid in the pharmaceutical composition is greater than about 1 percent by weight of the pharmaceutical composition.

In one embodiment, the amount of phospholipid in the pharmaceutical composition is greater than about 2 percent by weight of the pharmaceutical composition.

Typically, the greater the concentration of the phospholipid in the pharmaceutical composition the higher the viscosity of the pharmaceutical composition. Accordingly, it is possible to vary the viscosity of the pharmaceutical composition by varying the amount of the phospholipid present in the pharmaceutical composition.

One of ordinary skill in the art will recognize, however, that the amount of phospholipid present in the pharmaceutical compositions of the invention can vary widely depending on the organic solvents present, the pharmaceutically active agent present, and/or other additional components present in the pharmaceutical composition.

The phospholipids are commercially available or can be obtained by methods well known to those skilled in the art. Representative methods for obtaining phospholipids are described in Sandra Pesch et al., *Properties of Unusual Phospholipids Bearing Acetylenic Fatty Acids*, Tettrahedron, vol. 15, no. 43, 14,627-14634 (1997); Sepp D. Kohlwein, *Phospholipid Synthesis, Sorting, Subcellular Traffic—The Yeast Approach*, Trends in Cell Biology, vol. 6, 260-266 (1996), Serguei V. Vinogradov, *Synthesis of Phospholipids—Oligodeoxyribonucleotide Conjugates*, Tett. Lett., vol. 36, no. 14, 2493-2496 (1995), and references cited therein.

4.3 The Sphingomyelin

Any pharmaceutically acceptable sphingomyelin can be used in the pharmaceutical compositions of the invention.

In one embodiment, the sphingomyelin is

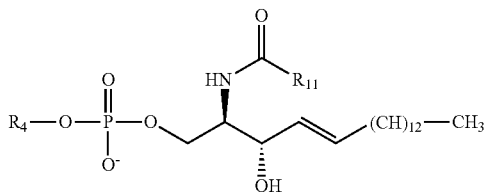

wherein $R_{11}$ is a $C_1$-$C_{24}$ linear, saturated or unsaturated hydrocarbon and $R_4$ is —$CH_2CH_2N(CH_3)_3^+$. In another embodiment, $R_{11}$ is a $C_8$-$C_{24}$ linear, saturated or unsaturated hydrocarbon and $R_4$ is —$CH_2CH_2N(CH_3)_3^+$. In another embodiment, $R_{11}$ is a $C_{16}$-$C_{24}$ linear, saturated or unsaturated hydrocarbon and $R_4$ is —$CH_2CH_2N(CH_3)_3^+$.

Suitable sphingomyelins include, but are not limited to, C2-Sphingomyelin, C6-Sphingomyelin, C18-Sphingomyelin, C6-NBD-Sphingomyelin, and C12-NBD Sphingomyelin, commercially available from Avant Polar Lipids Inc. of Alabaster, Ala.

4.4 The Pharmaceutically Active Agent

Any pharmaceutically active agent that is compatible with the phospholipid or sphingomyelin and the polar aprotic organic solvent and polar protic organic solvent or that is compatible with the phospholipid or sphingomyelin and the propylene glycol substantially free of other organic solvents or glycerol formal substantially free of other organic solvents can be used in the pharmaceutical compositions according to the invention.

In one embodiment, the pharmaceutically active agent is present as a pharmaceutically acceptable salt of the pharmaceutically active agent.

In one embodiment, the pharmaceutically active agent is a zwitterion.

In one embodiment, the pharmaceutically active agent is a basic compound.

In one embodiment, the pharmaceutically active agent is an acidic compound.

In one embodiment, the pharmaceutically active agent is a neutral compound.

The amount of pharmaceutically active agent in the pharmaceutical compositions typically ranges from about 0.01 to 30 percent by weight of the pharmaceutical composition.

In one embodiment, the pharmaceutically active agent in the pharmaceutical compositions ranges from about 0.01 to 25 percent by weight of the pharmaceutical composition.

In one embodiment, the pharmaceutically active agent in the pharmaceutical compositions ranges from about 0.01 to 20 percent by weight of the pharmaceutical composition.

In one embodiment, the pharmaceutically active agent in the pharmaceutical compositions ranges from about 0.01 to 15 percent by weight of the pharmaceutical composition.

The amount of pharmaceutically active agent in the pharmaceutical compositions typically ranges from about 0.01 to 10 percent by weight of the pharmaceutical composition.

In one embodiment, the pharmaceutically active agent in the pharmaceutical compositions ranges from about 0.05 to 7.5 percent by weight of the pharmaceutical composition.

In one embodiment, the amount of pharmaceutically active agent in the pharmaceutical composition is from about 0.05 to 5 percent by weight of the pharmaceutical composition.

In one embodiment, the amount of pharmaceutically active agent in the pharmaceutical composition is from about 0.1 to 3 percent by weight of the pharmaceutical composition.

In one embodiment, the amount of pharmaceutically active agent in the pharmaceutical composition is from about 0.1 to 2 percent by weight of the pharmaceutical composition.

In one embodiment, the amount of pharmaceutically active agent in the pharmaceutical composition is from about 0.1 to 1 percent by weight of the pharmaceutical composition.

One of ordinary skill in the art will recognize, however, that the amount of pharmaceutically active agent in the pharmaceutical compositions according to the invention can vary widely depending on the pharmaceutically active agent and any other components present in the pharmaceutical composition.

Examples of pharmaceutically active agents useful in the composition and methods of the invention include, but are not limited to, α-adrenergic agonists, β-adrenergic agonists, α-adrenergic blockers, β-adrenergic blockers, aldose reductase inhibitors, anabolics, analgesics (narcotic and non-narcotic), androgens, anesthetics, anorexics, anthelmintics (e.g., cestode, nematode, onchocerca, schistosoma, and the like), anti-allergics, anti-ameboics, anti-yeast agents, anti-androgens, anti-anginals, anti-arrhythmics, anti-arteriosclerotics, anti-arthritics, antibiotics and other antibacterials, anti-cholinergics, anti-convulsants, anti-depressants, anti-diabetics agents, anti-diarrheals, anti-diuretics, anti-estrogens, antifungals, anti-glaucomas, anti-gonadotropins, anti-gout agents, anti-histaminics, anti-hyperlipoproteinemics, anti-hypertensives, anti-hyperthyroid agents, anti-hypertrophy agents, anti-hypotensives, anti-hypothyroid agents, antiinflammatories, anti-malarials, antimicrobials, anti-migraine agents, anti-nausea agents, anti-neoplastics, antioxidants, antiparasitic agents, anti-parkinsonian agents, anti-pheochromocytoma agents, anti-pneumocytis agents, antiproliferative agents, anti-protozoals (e.g., leishmania, trichomonas, trypansoma, and the like), anti-pruritic agents, anti-psoratic agents, anti-psychotic agents, anti-pyretics, anti-rheumatics, anti ricketts agents, anti-seborrheic agents, antiseptics, antispasmodic agents, anti-thrombotic agents, antitussives, anti-ulcer agents, anti-urolithic agents, anti-venins, antivirals, anxiolytics, benzodiazepine antagonists, bronchodilators, calcium channel blockers, calcium regulators, cardiotonics, chelating agents, chemotherapeutics, cholecystokinin antagonists, cholelitholytic agents, choleretics, cholinergics, cholinesterase inhibitors, cholinesterase reactivators, central nervous system stimulants and agents, decongestants, diuretics, dopamine receptor agonists, drugs for treating or preventing pain, ectoparasiticides, enzymes, enzyme inducers, estrogens, gastric secretion inhibitors, glucocorticoids, gonad-stimulating principles, gonadotropic hormones, growth hormones, growth hormone releasing factors, growth stimulants, hemolytics, heparin agonists, hepatoprotectants, hypnotics, immune system boosters, immunomodulators, immunosuppressants, lactation stimulating hormones, LH-RH stimulating agonists, lipotropics, lupus erythmatosus suppressants, mineral corticoids, miotics, monoamine oxidase inhibitors, mucolytics, muscle relaxants, narcotic antagonists, neuroprotectives, neotropics, ovarian hormones, oxytocics, pepsin inhibitors, peristaltic stimulators, progestrogens, prolactin inhibitors, protoglandins, prostoglandin analogs, protease inhibitors, respiratory stimulants, sclerosing agents, sedatives, steroids, thrombolytics, thyrotropic hormones, transdermal penetration enhancers, uricosurics, vasoconstrictors, vasodilators (e.g., cerebral, coronary, peropheral, and the like), vasoprotectants, vitamins, vitamin source extracts, vulneraries (including, but not limited to, those listed in U.S. Pat. No. 5,719,197, the entire disclosure of which is incorporated herein by reference), and combinations thereof. Other additionally or alternately acceptable pharmaceutically active agents can be found, e.g., in U.S. Pat. No. 6,221,383, the entire disclosure of which is incorporated herein by reference.

In one embodiment, the pharmaceutically active agent comprises an antibacterial agent.

In one embodiment, the pharmaceutically active agent comprises an antifungal agent.

In one embodiment, the pharmaceutically active agent comprises an antiparasitic agent.

In one embodiment, the pharmaceutically active agent comprises an anti-yeast agent.

In one embodiment, the pharmaceutically active agent comprises an antiviral agent.

In one embodiment, the pharmaceutically active agent comprises a hormone.

In one embodiment, the pharmaceutically active agent comprises a antiinflammatory agent.

In one embodiment, the pharmaceutically active agent comprises a steroid.

Examples of useful antibacterial agents include, but are not limited to, β-lactam antibiotics such as penicillins, amoxicillin, ampicillin, and cephalosporins; macrolide antibiotics such as oleandomycin and erythromycin; tetracyclines such as tetracycline, oxytetracycline, and chlortetracycline; procaine penicillin G; quinolones such as enrofloxacin, nalidixic acid, and norfloxacin; sulfonamides; chloramphenicol; florfenicol; thiamphenicol, aminoglycosides such as tobramycin, streptomycin, kanamycin, azithromycin, and gentamicin; nucleoside antibiotics such as polyoxin B; actinorhodine; bacitracin; candicidin A; ceftiofor; clindamycin; cycloheximide; cycloserine; fosfomycin; griseofulvin; metronidazole; monensin; novobiocin; rifampin; streptothricin; tetranactin; tilmicosin; tylosin; actinomycin D; adriamycin; bleomycin B2; glycolipids such as moenomycin A; mitomycin C; nojirimycin; valinomycin; and vancomycin; (See, e.g., Bradford P. Smith, *Large Animal Internal Medicine,* 2nd edn., Mosby, St. Louis, 1996, p. 644, and S. Birchard and R. Sherding, *Saunders Manual of Small Animal Practice*, W.B. Saunders Company, Philadelphia, 1994, p. 739).

Examples of useful antifungal agents include, but are not limited to, terbinafine amphotericin B, ketaconazole, clotrimazole, miconazole, 5-fluorocytosine, enilconazole, itraconazole, thiabendazole, and iodides (See, e.g., Bradford P. Smith, *Large Animal Internal Medicine,* 2nd edn., Mosby, St. Louis, 1996, p. 576, and S. Birchard and R. Sherding, *Saunders Manual of Small Animal Practice*, W.B. Saunders Company, Philadelphia, 1994, p. 576).

Examples of useful antiviral agents include, but are not limited to, interferon (See, e.g., Bradford P. Smith, *Large Animal Internal Medicine,* 2nd edn., Mosby, St. Louis, 1996, p. 646).

Examples of useful antiparasitic agents include, but are not limited to, benzimidazoles, such as thiabendazole, fenbendazole, mebendazole, nitazoxanide (NTZ), oxfendazole, oxibendazole, albendazole, parbendazole, and febantel; tetrahydropyridines such as morantel tartrate/pyrantel pamoate); levamisole, organophosphates such as haloxon, coumaphos, trichlorfon, and dichlorvos; piperazine salts; ivermectin; and phenothiazine (See, e.g., Bradford P. Smith, *Large Animal Internal Medicine,* 2nd edn., Mosby, St. Louis, 1996, p. 1688).

Examples of useful antiinflammatory agents include, but are not limited to, steroids such as betamethazone; corticosteroids such as dexamethasone; antihistamines; and non-steroidal antiinflammatory drugs such as aspirin, flunixin meglumine, phenylbutazone, diclofenac, and ibuprofin (See, e.g., Bradford P. Smith, *Large Animal Internal Medicine,* 2nd edn., Mosby, St. Louis, 1996, p. 645).

Examples of useful anti-yeast agents include, but are not limited to, aminoglycosides such as tobramycin, streptomycin, kanamycin, and gentamicin.

In one embodiment, the pharmaceutically active agent comprises gentamicin.

In one embodiment, the pharmaceutically active agent comprises azithromycin.

In one embodiment, the pharmaceutically active agent comprises tobramycin.

In one embodiment, the pharmaceutically active agent comprises tobramycin decanoic acid salt.

In one embodiment, the pharmaceutically active agent comprises tobramycin oleic acid salt.

In one embodiment, the pharmaceutically active agent comprises tobramycin acetic acid salt.

In one embodiment, the pharmaceutically active agent comprises terbinafine.

In one embodiment, the pharmaceutically active agent comprises terbinafine decanoic acid salt.

In one embodiment, the pharmaceutically active agent comprises terbinafine oleic acid salt.

In one embodiment, the pharmaceutically active agent comprises terbinafine acetic acid salt.

In one embodiment, the pharmaceutically active agent comprises betamethazone.

In one embodiment, the pharmaceutically active agent comprises florfenicol.

In one embodiment, the pharmaceutically active agent comprises thiamphenicol.

In one embodiment, the pharmaceutically active agent comprises clotrimazole.

In one embodiment, the pharmaceutically active agent comprises tilmicosin.

In one embodiment, the pharmaceutically active agent comprises a tetracycline compound.

In one embodiment, the pharmaceutically active agent comprises ketoconazole.

In one embodiment, the pharmaceutically active agent comprises diclofenac.

In one embodiment, the pharmaceutically active agent comprises flunixin.

In one embodiments, there can be multiple pharmaceutically active agents in a single pharmaceutical composition.

In one embodiment, the pharmaceutically active agent comprises the combination of an antibacterial agent, an antifungal agent, and a steroid.

Effective amounts of these pharmaceutically active agents are known to those skilled in the art. It is well within the skilled artisan's purview to determine each pharmaceutically active agent's optimal effective-amount range.

In one embodiment of the invention, where multiple pharmaceutically active agents are administered to an animal, the effective amount of each pharmaceutically active agent is less than its effective amount would be were the other pharmaceutically active agent(s) not administered. In this case, without being bound by theory, it is believed that multiple pharmaceutically active agents can be chosen to act synergistically to treat or prevent a condition (e.g., a bacterial infection).

In one embodiment, the pharmaceutically active agent comprises a combination of tobramycin, terbinafine, and betamethazone.

In one embodiment, the pharmaceutically active agent comprises a combination of tobramycin decanoic acid salt, terbinafine decanoic acid salt, and betamethazone.

In one embodiment, the pharmaceutically active agent has an amine moiety and is present in the pharmaceutical composition of the invention as a fatty acid salt ("FAS") by converting the amine moiety to an ammonium cation whose counterion is a fatty acid moiety such as those described in International Publication No. WO 03/034988 A2, the entire disclosure of which is incorporated herein in its entirety.

Without being bound to theory, it is believed that a FAS of a pharmaceutically active agent provides additional sustained- or controlled-release of the pharmaceutically active agent (as reflected in more steady blood levels as a function of time). Without wishing to be bound by theory, it is believed that the additional sustained- or controlled-release of the pharmaceutically active agent obtained when using a FAS of a pharmaceutically active agent is because the FAS of a pharmaceutically active agent is less soluble in water than the pharmaceutically active agent itself or other non-fatty acid salt of the pharmaceutically active agent and, accordingly, is absorbed by the animal more slowly.

In one embodiment, the FAS salt of the pharmaceutically active agent is a salt of a $C_6$-$C_{18}$ carboxylic acid.

In one embodiment, the FAS salt of the pharmaceutically active agent is a salt of a $C_8$-$C_{18}$ carboxylic acid.

In one embodiment, the FAS salt of the pharmaceutically active agent is a salt of a $C_{10}$-$C_{18}$ carboxylic acid.

In one embodiment, the FAS salt of the pharmaceutically active agent is a salt of a linear unsaturated fatty acid.

In one embodiment, the FAS salt of the pharmaceutically active agent is a salt of a linear saturated fatty acid.

4.5 Pharmaceutical Compositions 4.5.1 Pharmaceutical Compositions Comprising (i) a Phospholipid or Spingomyelin, (ii) a First Organic Solvent, (iii) a Second Organic Solvent, and (iv) a Therapeutically Effective Amount of a Pharmaceutically Active Agent Any pharmaceutically active agent described above can be used in the pharmaceutical compositions.

Any phospholipid or sphingomyelin described above can be used in the pharmaceutical compositions.

4.5.1.1 The First Organic Solvent and Second Organic Solvent

Any pharmaceutically acceptable organic solvents can be used in the pharmaceutical compositions of the invention. The first organic solvent and the second organic solvent, however, must be miscible.

Suitable organic solvents can include small amounts of impurities. Typically, the organic solvents have a purity of greater than 95 percent by weight, preferably greater than 97 percent by weight, more preferably greater than 98 percent by weight, and most preferably greater than 99 percent by weight.

In one embodiment, the organic solvents are designated as GRAS ("generally recognized as safe") by the FDA for use or consumption by animals.

In another embodiment, the organic solvents are designated as GRAS by the FDA for use or consumption by humans.

In one embodiment, the first organic solvent is a polar aprotic solvent and the second organic solvent is a polar protic solvent.

Representative polar aprotic solvents useful in the compositions and methods of the invention include, but are not limited to, propylene carbonate, dimethyl sulfoxide (DMSO), dimethyl acetamide (DMA), dimethyl formamide (DMF), triacetin, and N-methyl-2-pyrrolidone (NMP).

Representative polar aprotic solvents useful in the compositions and methods of the invention include, but are not limited to, glycerol formal and diols such as propylene glycol, and 1,4-butane diol When the first organic solvent is a polar aprotic solvent and the second organic solvent is a polar protic solvent, the ratio of the first organic solvent to the second organic solvent can ranges from about 90:10 to 10:90. In one embodiment, the ratio of the first organic solvent to the second organic solvent ranges from about 80:20 to 20:80. In one embodiment, the ratio of the first organic solvent to the second organic solvent ranges from about 70:30 to 30:70. In one embodiment, the ratio of the first organic solvent to the second organic solvent ranges from about 60:40 to 40:60. In one embodiment, the ratio of the first organic solvent to the second organic solvent is about 50:50.

In one embodiment, the first organic solvent and the second organic solvent are each substantially free of water. Organic solvents that are substantially free of water are advantageous since they are not conducive to bacterial growth. Accordingly, it is typically not necessary to include a preservative in pharmaceutical compositions that are substantially free of water. However, in some embodiments, the non-aqueous pharmaceutical composition of the invention can contain a preservative.

In one embodiment, the first organic solvent is propylene carbonate and the second organic solvent is glycerol formal.

In one embodiment, the first organic solvent is propylene carbonate and the second organic solvent is propylene glycol.

In one embodiment, the first organic solvent is propylene carbonate and the second organic solvent is glycerol formal glycol or propylene glycol and the ratio of the first organic solvent to the second organic solvent ranges from about 80:20 to about 20:80.

In one embodiment, the first organic solvent is propylene carbonate and the second organic solvent is glycerol formal or propylene glycol and the ratio of the first organic solvent to the second organic solvent ranges from about 75:25 to about 25:75.

In one embodiment, the first organic solvent is propylene carbonate and the second organic solvent is glycerol formal or propylene glycol and the ratio of the first organic solvent to the second organic solvent ranges from about 60:40 to about 40:60.

In one embodiment, the first organic solvent is propylene carbonate and the second organic solvent is glycerol formal or propylene glycol and the ratio of the first organic solvent to the second organic solvent ranges from about 50:50.

The total amount of organic solvent (i.e., the first organic solvent and the second organic solvent) in the pharmaceutical composition typically ranges from about 20 to about 99 percent by weight of the pharmaceutical composition.

In one embodiment, the total amount of organic solvent in the pharmaceutical composition is from about 35 to about 90 percent by weight of the pharmaceutical composition.

In one embodiment, the amount of organic solvent in the pharmaceutical composition is at least about 35 percent by weight of the pharmaceutical composition.

In one embodiment, the amount of organic solvent in the pharmaceutical composition is at least about 50 percent by weight of the pharmaceutical composition.

In one embodiment, the amount of organic solvent in the pharmaceutical composition is at least about 75 percent by weight of the pharmaceutical composition.

In one embodiment, the amount of organic solvent in the pharmaceutical composition is at least about 85 percent by weight of the pharmaceutical composition.

4.5.1.2 Representative Pharmaceutical Formulations

In one embodiment, the first organic solvent is propylene carbonate, the second organic solvent is glycerol formal, and the phospholipid is

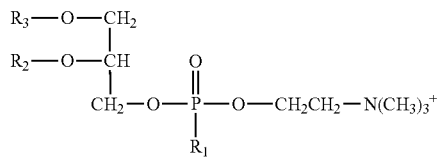

wherein $R_2$ and $R_3$ each are a stearoyl group or a palmitoyl group and the ratio of total stearoyl groups to palmitoyl groups is about 85:15 and $R_1$ is $O^-$ (Phospholipon® 90H, commercially available from Phospholipid GmbH of Cologne, Germany).

In one embodiment, the first organic solvent is propylene carbonate, the second organic solvent is glycerol formal, the phospholipid is Phospholipon® 90H, and the ratio of the propylene carbonate to the glycerol formal ranges from about 60:40 to 40:60.

In one embodiment, the first organic solvent is propylene carbonate, the second organic solvent is glycerol formal, the phospholipid is Phospholipon® 90H, and the ratio of the propylene carbonate to the glycerol formal is about 50:50.

In one embodiment, the first organic solvent is propylene carbonate, the second organic solvent is glycerol formal, the phospholipid is Phospholipon® 90H, the ratio of the propylene carbonate to the glycerol formal ranges from about 60:40 to 40:60, and the phospholipid is present in an amount of about 1 to 4 percent by weight of the pharmaceutical composition.

In one embodiment, the first organic solvent is propylene carbonate, the second organic solvent is glycerol formal, the phospholipid is Phospholipon® 90H, the ratio of the propylene carbonate to the glycerol formal is about 50:50, and the phospholipid is present in an amount of about 1 to 4 percent by weight of the pharmaceutical composition.

In one embodiment, the first organic solvent is propylene carbonate, the second organic solvent is glycerol formal, the phospholipid is Phospholipon® 90H, the ratio of the propylene carbonate to the glycerol formal ranges from about 60:40 to 40:60, and the phospholipid is present in an amount of about 3 percent by weight of the pharmaceutical composition.

In one embodiment, the first organic solvent is propylene carbonate, the second organic solvent is glycerol formal, the phospholipid is Phospholipon® 90H, the ratio of the propylene carbonate to the glycerol formal is about 50:50, and the phospholipid is present in an amount of about 3 percent by weight of the pharmaceutical composition.

In one embodiment, the first organic solvent is propylene carbonate, the second organic solvent is glycerol formal, the phospholipid is Phospholipon® 90H, and the pharmaceutically active compound is at least one of an antibacterial agent, an antifungal agent, or a steroid.

In one embodiment, the first organic solvent is propylene carbonate, the second organic solvent is glycerol formal, the phospholipid is Phospholipon® 90H, the ratio of the propylene carbonate to the glycerol formal ranges from about 60:40 to 40:60, and the pharmaceutically active compound is at least one of an antibacterial agent, an antifungal agent, or a steroid.

In one embodiment, the first organic solvent is propylene carbonate, the second organic solvent is glycerol formal, the phospholipid is Phospholipon® 90H, the ratio of the propylene carbonate to the glycerol formal is about 50:50, and the pharmaceutically active compound is at least one of an antibacterial agent, an antifungal agent, or a steroid.

In one embodiment, the first organic solvent is propylene carbonate, the second organic solvent is glycerol formal, the phospholipid is Phospholipon® 90H, the ratio of the propylene carbonate to the glycerol formal ranges from about 60:40 to 40:60, the phospholipid is present in an amount of about 1 to 4 percent by weight of the pharmaceutical composition, and the pharmaceutically active compound is at least one of an antibacterial agent, an antifungal agent, or a steroid.

In one embodiment, the first organic solvent is propylene carbonate, the second organic solvent is glycerol formal, the phospholipid is Phospholipon® 90H, the ratio of the propylene carbonate to the glycerol formal is about 50:50, the phospholipid is present in an amount of about 1 to 4 percent by weight of the pharmaceutical composition, and the pharmaceutically active compound is at least one of an antibacterial agent, an antifungal agent, or a steroid.

In one embodiment, the first organic solvent is propylene carbonate, the second organic solvent is glycerol formal, the phospholipid is Phospholipon® 90H, the ratio of the propylene carbonate to the glycerol formal ranges from about 60:40 to 40:60, the phospholipid is present in an amount of about 3 percent by weight of the pharmaceutical composition, and the pharmaceutically active compound is at least one of an antibacterial agent, an antifungal agent, or a steroid.

In one embodiment, the first organic solvent is propylene carbonate, the second organic solvent is glycerol formal, the phospholipid is Phospholipon® 90H, the ratio of the propylene carbonate to the glycerol formal is about 50:50, the phospholipid is present in an amount of about 3 percent by weight of the pharmaceutical composition, and the pharmaceutically active compound is at least one of an antibacterial agent, an antifungal agent, or a steroid.

In one embodiment, the first organic solvent is propylene carbonate, the second organic solvent is glycerol formal, the phospholipid is Phospholipon® 90H, and the pharmaceutically active compound comprises an antibacterial agent, an antifungal agent, and a steroid.

In one embodiment, the first organic solvent is propylene carbonate, the second organic solvent is glycerol formal, the phospholipid is Phospholipon® 90H, the ratio of the propylene carbonate to the glycerol formal ranges from about 60:40 to 40:60, and the pharmaceutically active compound comprises an antibacterial agent, an antifungal agent, and a steroid.

In one embodiment, the first organic solvent is propylene carbonate, the second organic solvent is glycerol formal, the phospholipid is Phospholipon® 90H, the ratio of the propylene carbonate to the glycerol formal is about 50:50, and the pharmaceutically active compound comprises an antibacterial agent, an antifungal agent, and a steroid.

In one embodiment, the first organic solvent is propylene carbonate, the second organic solvent is glycerol formal, the phospholipid is Phospholipon® 90H, the ratio of the propylene carbonate to the glycerol formal ranges from about 60:40 to 40:60, the phospholipid is present in an amount of about 1 to 4 percent by weight of the pharmaceutical composition, and the pharmaceutically active compound comprises an antibacterial agent, an antifungal agent, and a steroid.

In one embodiment, the first organic solvent is propylene carbonate, the second organic solvent is glycerol formal, the phospholipid is Phospholipon® 90H, the ratio of the propylene carbonate to the glycerol formal is about 50:50, the phospholipid is present in an amount of about 1 to 4 percent by weight of the pharmaceutical composition, and the pharmaceutically active compound comprises an antibacterial agent, an antifungal agent, and a steroid.

In one embodiment, the first organic solvent is propylene carbonate, the second organic solvent is glycerol formal, the phospholipid is Phospholipon® 90H, the ratio of the propylene carbonate to the glycerol formal ranges from about 60:40 to 40:60, the phospholipid is present in an amount of about 3 percent by weight of the pharmaceutical composition, and the pharmaceutically active compound comprises antibacterial agent, an antifungal agent, and a steroid.

In one embodiment, the first organic solvent is propylene carbonate, the second organic solvent is glycerol formal, the phospholipid is Phospholipon® 90H, the ratio of the propylene carbonate to the glycerol formal is about 50:50, the phospholipid is present in an amount of about 3 percent by weight of the pharmaceutical composition, and the pharmaceutically active compound comprises antibacterial agent, an antifungal agent, and a steroid.

In one embodiment, the first organic solvent is propylene carbonate, the second organic solvent is glycerol formal, the phospholipid is Phospholipon® 90H, and the pharmaceutically active compound comprises tobramycin or a pharmaceutically acceptable salt thereof, terbinafine or a pharmaceutically acceptable salt thereof, and betamethasone or a pharmaceutically acceptable ester thereof.

In one embodiment, the first organic solvent is propylene carbonate, the second organic solvent is glycerol formal, the phospholipid is Phospholipon® 90H, the ratio of the propylene carbonate to the glycerol formal ranges from about 60:40 to 40:60, and the pharmaceutically active compound comprises tobramycin or a pharmaceutically acceptable salt thereof, terbinafine or a pharmaceutically acceptable salt thereof, and betamethasone or a pharmaceutically acceptable ester thereof.

In one embodiment, the first organic solvent is propylene carbonate, the second organic solvent is glycerol formal, the phospholipid is Phospholipon® 90H, the ratio of the propylene carbonate to the glycerol formal is about 50:50, and the pharmaceutically active compound comprises tobramycin or a pharmaceutically acceptable salt thereof, terbinafine or a pharmaceutically acceptable salt thereof, and betamethasone or a pharmaceutically acceptable ester thereof.

In one embodiment, the first organic solvent is propylene carbonate, the second organic solvent is glycerol formal, the phospholipid is Phospholipon® 90H, the ratio of the propylene carbonate to the glycerol formal ranges from about 60:40 to 40:60, the phospholipid is present in an amount of about 1 to 4 percent by weight of the pharmaceutical composition, and the pharmaceutically active compound comprises tobramycin or a pharmaceutically acceptable salt thereof, terbinafine or a pharmaceutically acceptable salt thereof, and betamethasone or a pharmaceutically acceptable ester thereof.

In one embodiment, the first organic solvent is propylene carbonate, the second organic solvent is glycerol formal, the phospholipid is Phospholipon® 90H, the ratio of the propylene carbonate to the glycerol formal is about 50:50, the phospholipid is present in an amount of about 1 to 4 percent by weight of the pharmaceutical composition, and the pharmaceutically active compound comprises tobramycin or a pharmaceutically acceptable salt thereof, terbinafine or a pharmaceutically acceptable salt thereof, and betamethasone or a pharmaceutically acceptable ester thereof.

In one embodiment, the first organic solvent is propylene carbonate, the second organic solvent is glycerol formal, the phospholipid is Phospholipon® 90H, the ratio of the propylene carbonate to the glycerol formal ranges from about 60:40 to 40:60, the phospholipid is present in an amount of about 3 percent by weight of the pharmaceutical composition, and the pharmaceutically active compound comprises tobramycin or a pharmaceutically acceptable salt thereof, terbinafine or a pharmaceutically acceptable salt thereof, and betamethasone or a pharmaceutically acceptable ester thereof.

In one embodiment, the first organic solvent is propylene carbonate, the second organic solvent is glycerol formal, the phospholipid is Phospholipon® 90H, the ratio of the propylene carbonate to the glycerol formal is about 50:50, the phospholipid is present in an amount of about 3 percent by weight of the pharmaceutical composition, and the pharmaceutically active compound comprises tobramycin or a pharmaceutically acceptable salt thereof, terbinafine or a pharmaceutically acceptable salt thereof, and betamethasone or a pharmaceutically acceptable ester thereof.

In one embodiment, the first organic solvent is propylene carbonate, the second organic solvent is glycerol formal, the phospholipid is Phospholipon® 90H, and the pharmaceutically active compound comprises tobramycin or a pharmaceutically acceptable salt thereof in an amount of about 1 to 3 percent by weight of the pharmaceutical composition, terbinafine or a pharmaceutically acceptable salt thereof in an amount of about 1 to 3 percent by weight of the pharmaceutical composition, and betamethasone or a pharmaceutically acceptable ester thereof in an amount of about 0.05 to 0.3 percent by weight of the pharmaceutical composition.

In one embodiment, the first organic solvent is propylene carbonate, the second organic solvent is glycerol formal, the phospholipid is Phospholipon® 90H, the ratio of the propylene carbonate to the glycerol formal ranges from about 60:40 to 40:60, and the pharmaceutically active compound comprises tobramycin or a pharmaceutically acceptable salt thereof in an amount of about 1 to 3 percent by weight of the pharmaceutical composition, terbinafine or a pharmaceutically acceptable salt thereof in an amount of about 1 to 3 percent by weight of the pharmaceutical composition, and betamethasone or a pharmaceutically acceptable ester thereof in an amount of about 0.05 to 0.3 percent by weight of the pharmaceutical composition.

In one embodiment, the first organic solvent is propylene carbonate, the second organic solvent is glycerol formal, the phospholipid is Phospholipon® 90H, the ratio of the propylene carbonate to the glycerol formal is about 50:50, and the pharmaceutically active compound comprises tobramycin or a pharmaceutically acceptable salt thereof in an amount of about 1 to 3 percent by weight of the pharmaceutical composition, terbinafine or a pharmaceutically acceptable salt thereof in an amount of about 1 to 3 percent by weight of the pharmaceutical composition, and betamethasone or a pharmaceutically acceptable ester thereof in an amount of about 0.05 to 0.3 percent by weight of the pharmaceutical composition.

In one embodiment, the first organic solvent is propylene carbonate, the second organic solvent is glycerol formal, the phospholipid is Phospholipon® 90H, the ratio of the propylene carbonate to the glycerol formal ranges from about 60:40 to 40:60, the phospholipid is present in an amount of about 1 to 4 percent by weight of the pharmaceutical composition, and the pharmaceutically active compound comprises tobramycin or a pharmaceutically acceptable salt thereof in an amount of about 1 to 3 percent by weight of the pharmaceutical composition, terbinafine or a pharmaceutically acceptable salt thereof in an amount of about 1 to 3 percent by weight of the pharmaceutical composition, and betamethasone or a pharmaceutically acceptable ester thereof in an amount of about 0.05 to 0.3 percent by weight of the pharmaceutical composition.

In one embodiment, the first organic solvent is propylene carbonate, the second organic solvent is glycerol formal, the phospholipid is Phospholipon® 90H, the ratio of the propylene carbonate to the glycerol formal is about 50:50, the phospholipid is present in an amount of about 1 to 4 percent by weight of the pharmaceutical composition, and the pharmaceutically active compound comprises tobramycin or a pharmaceutically acceptable salt thereof in an amount of about 1 to 3 percent by weight of the pharmaceutical composition, terbinafine or a pharmaceutically acceptable salt thereof in an amount of about 1 to 3 percent by weight of the pharmaceutical composition, and betamethasone or a pharmaceutically acceptable ester thereof in an amount of about 0.05 to 0.3 percent by weight of the pharmaceutical composition.

In one embodiment, the first organic solvent is propylene carbonate, the second organic solvent is glycerol formal, the phospholipid is Phospholipon® 90H, the ratio of the propylene carbonate to the glycerol formal ranges from about 60:40 to 40:60, the phospholipid is present in an amount of about 3 percent by weight of the pharmaceutical composition, and the pharmaceutically active compound comprises tobramycin or a pharmaceutically acceptable salt thereof in an amount of about 1 to 3 percent by weight of the pharmaceutical composition, terbinafine or a pharmaceutically acceptable salt thereof in an amount of about 1 to 3 percent by weight of the pharmaceutical composition, and betamethasone or a pharmaceutically acceptable ester thereof in an amount of about 0.05 to 0.3 percent by weight of the pharmaceutical composition.

In one embodiment, the first organic solvent is propylene carbonate, the second organic solvent is glycerol formal, the phospholipid is Phospholipon® 90H, the ratio of the propylene carbonate to the glycerol formal is about 50:50, the phospholipid is present in an amount of about 3 percent by weight of the pharmaceutical composition, and the pharmaceutically active compound comprises tobramycin or a pharmaceutically acceptable salt thereof in an amount of about 1 to 3 percent by weight of the pharmaceutical composition, terbinafine or a pharmaceutically acceptable salt thereof in an amount of about 1 to 3 percent by weight of the pharmaceutical composition, and betamethasone or a pharmaceutically acceptable ester thereof in an amount of about 0.05 to 0.3 percent by weight of the pharmaceutical composition.

In one embodiment, the first organic solvent is propylene carbonate, the second organic solvent is glycerol formal, the phospholipid is Phospholipon® 90H, and the pharmaceutically active compound comprises tobramycin or a pharmaceutically acceptable salt thereof in an amount of about 1 percent by weight of the pharmaceutical composition, terbinafine or a pharmaceutically acceptable salt thereof in an amount of about 1 percent by weight of the pharmaceutical composition, and betamethasone or a pharmaceutically acceptable ester thereof in an amount of about 0.1 percent by weight of the pharmaceutical composition.

In one embodiment, the first organic solvent is propylene carbonate, the second organic solvent is glycerol formal, the phospholipid is Phospholipon® 90H, the ratio of the propylene carbonate to the glycerol formal ranges from about 60:40 to 40:60, and the pharmaceutically active compound comprises tobramycin or a pharmaceutically acceptable salt thereof in an amount of about 1 percent by weight of the pharmaceutical composition, terbinafine or a pharmaceutically acceptable salt thereof in an amount of about 1 percent by weight of the pharmaceutical composition, and betamethasone or a pharmaceutically acceptable ester thereof in an amount of about 0.1 percent by weight of the pharmaceutical composition.

In one embodiment, the first organic solvent is propylene carbonate, the second organic solvent is glycerol formal, the phospholipid is Phospholipon® 90H, the ratio of the propylene carbonate to the glycerol formal is about 50:50, and the pharmaceutically active compound comprises tobramycin or a pharmaceutically acceptable salt thereof in an amount of about 1 percent by weight of the pharmaceutical composition, terbinafine or a pharmaceutically acceptable salt thereof in an amount of about 1 percent by weight of the pharmaceutical composition, and betamethasone or a pharmaceutically acceptable ester thereof in an amount of about 0.1 percent by weight of the pharmaceutical composition.

In one embodiment, the first organic solvent is propylene carbonate, the second organic solvent is glycerol formal, the phospholipid is Phospholipon® 90H, the ratio of the propylene carbonate to the glycerol formal ranges from about 60:40 to 40:60, the phospholipid is present in an amount of about 1 to 4 percent by weight of the pharmaceutical composition, and the pharmaceutically active compound comprises tobramycin or a pharmaceutically acceptable salt thereof in an amount of about 1 percent by weight of the pharmaceutical composition, terbinafine or a pharmaceutically acceptable salt thereof in an amount of about 1 percent by weight of the pharmaceutical composition, and betamethasone or a pharmaceutically acceptable ester thereof in an amount of about 0.1 percent by weight of the pharmaceutical composition.

In one embodiment, the first organic solvent is propylene carbonate, the second organic solvent is glycerol formal, the phospholipid is Phospholipon® 90H, the ratio of the propylene carbonate to the glycerol formal is about 50:50, the phospholipid is present in an amount of about 1 to 4 percent by weight of the pharmaceutical composition, and the pharmaceutically active compound comprises tobramycin or a pharmaceutically acceptable salt thereof in an amount of about 1 percent by weight of the pharmaceutical composition, terbinafine or a pharmaceutically acceptable salt thereof in an amount of about 1 percent by weight of the pharmaceutical composition, and betamethasone or a pharmaceutically acceptable ester thereof in an amount of about 0.1 percent by weight of the pharmaceutical composition.

In one embodiment, the first organic solvent is propylene carbonate, the second organic solvent is glycerol formal, the phospholipid is Phospholipon® 90H, the ratio of the propylene carbonate to the glycerol formal ranges from about 60:40 to 40:60, the phospholipid is present in an amount of about 3 percent by weight of the pharmaceutical composition, and the pharmaceutically active compound comprises tobramycin or a pharmaceutically acceptable salt thereof in an amount of about 1 percent by weight of the pharmaceutical composition, terbinafine or a pharmaceutically acceptable salt thereof in an amount of about 1 percent by weight of the pharmaceutical composition, and betamethasone or a pharmaceutically acceptable ester thereof in an amount of about 0.1 percent by weight of the pharmaceutical composition.

In one embodiment, the first organic solvent is propylene carbonate, the second organic solvent is glycerol formal, the phospholipid is Phospholipon® 90H, the ratio of the propylene carbonate to the glycerol formal is about 50:50, the phospholipid is present in an amount of about 3 percent by weight of the pharmaceutical composition, and the pharmaceutically active compound comprises tobramycin or a pharmaceutically acceptable salt thereof in an amount of about 1 percent by weight of the pharmaceutical composition, terbinafine or a pharmaceutically acceptable salt thereof in an amount of about 1 percent by weight of the pharmaceutical composition, and betamethasone or a pharmaceutically acceptable ester thereof in an amount of about 0.1 percent by weight of the pharmaceutical composition.

In one embodiment, the first organic solvent is propylene carbonate, the second organic solvent is glycerol formal, the phospholipid is Phospholipon® 90H, and the pharmaceutically active compound comprises florfenicol or a pharmaceutically acceptable ester thereof, terbinafine or a pharmaceutically acceptable salt thereof, and betamethasone or a pharmaceutically acceptable ester thereof.

In one embodiment, the first organic solvent is propylene carbonate, the second organic solvent is glycerol formal, the phospholipid is Phospholipon® 90H, the ratio of the propylene carbonate to the glycerol formal ranges from about 60:40 to 40:60, and the pharmaceutically active compound comprises florfenicol or a pharmaceutically acceptable ester thereof, terbinafine or a pharmaceutically acceptable salt thereof, and betamethasone or a pharmaceutically acceptable ester thereof.

In one embodiment, the first organic solvent is propylene carbonate, the second organic solvent is glycerol formal, the phospholipid is Phospholipon® 90H, the ratio of the propylene carbonate to the glycerol formal is about 50:50, and the pharmaceutically active compound comprises florfenicol or a pharmaceutically acceptable ester thereof, terbinafine or a pharmaceutically acceptable salt thereof, and betamethasone or a pharmaceutically acceptable ester thereof.

In one embodiment, the first organic solvent is propylene carbonate, the second organic solvent is glycerol formal, the phospholipid is Phospholipon® 90H, the ratio of the propylene carbonate to the glycerol formal ranges from about 60:40 to 40:60, the phospholipid is present in an amount of about 1 to 4 percent by weight of the pharmaceutical composition, and the pharmaceutically active compound comprises florfenicol or a pharmaceutically acceptable ester thereof, terbinafine or a pharmaceutically acceptable salt thereof, and betamethasone or a pharmaceutically acceptable ester thereof.

In one embodiment, the first organic solvent is propylene carbonate, the second organic solvent is glycerol formal, the phospholipid is Phospholipon® 90H, the ratio of the propylene carbonate to the glycerol formal is about 50:50, the phospholipid is present in an amount of about 1 to 4 percent by weight of the pharmaceutical composition, and the pharmaceutically active compound comprises florfenicol or a pharmaceutically acceptable ester thereof, terbinafine or a pharmaceutically acceptable salt thereof, and betamethasone or a pharmaceutically acceptable ester thereof.

In one embodiment, the first organic solvent is propylene carbonate, the second organic solvent is glycerol formal, the phospholipid is Phospholipon® 90H, the ratio of the propylene carbonate to the glycerol formal ranges from about 60:40 to 40:60, the phospholipid is present in an amount of about 3 percent by weight of the pharmaceutical composition, and the pharmaceutically active compound comprises florfenicol or a pharmaceutically acceptable ester thereof, terbinafine or a pharmaceutically acceptable salt thereof, and betamethasone or a pharmaceutically acceptable ester thereof.

In one embodiment, the first organic solvent is propylene carbonate, the second organic solvent is glycerol formal, the phospholipid is Phospholipon® 90H, the ratio of the propylene carbonate to the glycerol formal is about 50:50, the phospholipid is present in an amount of about 3 percent by weight of the pharmaceutical composition, and the pharmaceutically active compound comprises florfenicol or a pharmaceutically acceptable ester thereof, terbinafine or a pharmaceutically acceptable salt thereof, and betamethasone or a pharmaceutically acceptable ester thereof.

In one embodiment, the first organic solvent is propylene carbonate, the second organic solvent is glycerol formal, the phospholipid is Phospholipon® 90H, and the pharmaceutically active compound comprises florfenicol or a pharmaceutically acceptable ester thereof in an amount of about 1 to 3 percent by weight of the pharmaceutical composition, terbinafine or a pharmaceutically acceptable salt thereof in an amount of about 1 to 3 percent by weight of the pharmaceutical composition, and betamethasone or a pharmaceutically acceptable ester thereof in an amount of about 0.05 to 0.3 percent by weight of the pharmaceutical composition.

In one embodiment, the first organic solvent is propylene carbonate, the second organic solvent is glycerol formal, the phospholipid is Phospholipon® 90H, the ratio of the propylene carbonate to the glycerol formal ranges from about 60:40 to 40:60, and the pharmaceutically active compound comprises florfenicol or a pharmaceutically acceptable ester thereof in an amount of about 1 to 3 percent by weight of the pharmaceutical composition, terbinafine or a pharmaceutically acceptable salt thereof in an amount of about 1 to 3 percent by weight of the pharmaceutical composition, and betamethasone or a pharmaceutically acceptable ester thereof in an amount of about 0.05 to 0.3 percent by weight of the pharmaceutical composition.

In one embodiment, the first organic solvent is propylene carbonate, the second organic solvent is glycerol formal, the phospholipid is Phospholipon® 90H, the ratio of the propylene carbonate to the glycerol formal is about 50:50, and the pharmaceutically active compound comprises florfenicol or a pharmaceutically acceptable ester thereof in an amount of about 1 to 3 percent by weight of the pharmaceutical composition, terbinafine or a pharmaceutically acceptable salt thereof in an amount of about 1 to 3 percent by weight of the pharmaceutical composition, and betamethasone or a pharmaceutically acceptable ester thereof in an amount of about 0.05 to 0.3 percent by weight of the pharmaceutical composition.

In one embodiment, the first organic solvent is propylene carbonate, the second organic solvent is glycerol formal, the phospholipid is Phospholipon® 90H, the ratio of the propylene carbonate to the glycerol formal ranges from about 60:40 to 40:60, the phospholipid is present in an amount of about 1 to 4 percent by weight of the pharmaceutical composition, and the pharmaceutically active compound comprises florfenicol or a pharmaceutically acceptable ester thereof in an amount of about 1 to 3 percent by weight of the pharmaceutical composition, terbinafine or a pharmaceutically acceptable salt thereof in an amount of about 1 to 3 percent by weight of the pharmaceutical composition, and betamethasone or a pharmaceutically acceptable ester thereof in an amount of about 0.05 to 0.3 percent by weight of the pharmaceutical composition.

In one embodiment, the first organic solvent is propylene carbonate, the second organic solvent is glycerol formal, the phospholipid is Phospholipon® 90H, the ratio of the propylene carbonate to the glycerol formal is about 50:50, the phospholipid is present in an amount of about 1 to 4 percent by weight of the pharmaceutical composition, and the pharmaceutically active compound comprises florfenicol or a pharmaceutically acceptable ester thereof in an amount of about 1 to 3 percent by weight of the pharmaceutical composition, terbinafine or a pharmaceutically acceptable salt thereof in an amount of about 1 to 3 percent by weight of the pharmaceutical composition, and betamethasone or a pharmaceutically acceptable ester thereof in an amount of about 0.05 to 0.3 percent by weight of the pharmaceutical composition.

In one embodiment, the first organic solvent is propylene carbonate, the second organic solvent is glycerol formal, the phospholipid is Phospholipon® 90H, the ratio of the propylene carbonate to the glycerol formal ranges from about 60:40 to 40:60, the phospholipid is present in an amount of about 3 percent by weight of the pharmaceutical composition, and the pharmaceutically active compound comprises florfenicol or a pharmaceutically acceptable ester thereof in an amount of about 1 to 3 percent by weight of the pharmaceutical composition, terbinafine or a pharmaceutically acceptable salt thereof in an amount of about 1 to 3 percent by weight of the pharmaceutical composition, and betamethasone or a pharmaceutically acceptable ester thereof in an amount of about 0.05 to 0.3 percent by weight of the pharmaceutical composition.

In one embodiment, the first organic solvent is propylene carbonate, the second organic solvent is glycerol formal, the phospholipid is Phospholipon® 90H, the ratio of the propylene carbonate to the glycerol formal is about 50:50, the phospholipid is present in an amount of about 3 percent by weight of the pharmaceutical composition, and the pharmaceutically active compound comprises florfenicol or a pharmaceutically acceptable ester thereof in an amount of about 1 to 3 percent by weight of the pharmaceutical composition, terbinafine or a pharmaceutically acceptable salt thereof in an amount of about 1 to 3 percent by weight of the pharmaceutical composition, and betamethasone or a pharmaceutically acceptable ester thereof in an amount of about 0.05 to 0.3 percent by weight of the pharmaceutical composition.

In one embodiment, the first organic solvent is propylene carbonate, the second organic solvent is glycerol formal, the phospholipid is Phospholipon® 90H, and the pharmaceutically active compound comprises florfenicol or a pharmaceutically acceptable ester thereof in an amount of about 1 percent by weight of the pharmaceutical composition, terbinafine or a pharmaceutically acceptable salt thereof in an amount of about 1 percent by weight of the pharmaceutical composition, and betamethasone or a pharmaceutically acceptable ester thereof in an amount of about 0.1 percent by weight of the pharmaceutical composition.

In one embodiment, the first organic solvent is propylene carbonate, the second organic solvent is glycerol formal, the phospholipid is Phospholipon® 90H, the ratio of the propylene carbonate to the glycerol formal ranges from about 60:40 to 40:60, and the pharmaceutically active compound comprises florfenicol or a pharmaceutically acceptable ester thereof in an amount of about 1 percent by weight of the pharmaceutical composition, terbinafine or a pharmaceutically acceptable salt thereof in an amount of about 1 percent by weight of the pharmaceutical composition, and betamethasone or a pharmaceutically acceptable ester thereof in an amount of about 0.1 percent by weight of the pharmaceutical composition.

In one embodiment, the first organic solvent is propylene carbonate, the second organic solvent is glycerol formal, the phospholipid is Phospholipon® 90H, the ratio of the propylene carbonate to the glycerol formal is about 50:50, and the pharmaceutically active compound comprises florfenicol or a pharmaceutically acceptable ester thereof in an amount of about 1 percent by weight of the pharmaceutical composition, terbinafine or a pharmaceutically acceptable salt thereof in an amount of about 1 percent by weight of the pharmaceutical composition, and betamethasone or a pharmaceutically acceptable ester thereof in an amount of about 0.1 percent by weight of the pharmaceutical composition.

In one embodiment, the first organic solvent is propylene carbonate, the second organic solvent is glycerol formal, the phospholipid is Phospholipon® 90H, the ratio of the propylene carbonate to the glycerol formal ranges from about 60:40 to 40:60, the phospholipid is present in an amount of about 1 to 4 percent by weight of the pharmaceutical composition, and the pharmaceutically active compound comprises florfenicol or a pharmaceutically acceptable ester thereof in an amount of about 1 percent by weight of the pharmaceutical composition, terbinafine or a pharmaceutically acceptable salt thereof in an amount of about 1 percent by weight of the pharmaceutical composition, and betamethasone or a pharmaceutically acceptable ester thereof in an amount of about 0.1 percent by weight of the pharmaceutical composition.

In one embodiment, the first organic solvent is propylene carbonate, the second organic solvent is glycerol formal, the phospholipid is Phospholipon® 90H, the ratio of the propylene carbonate to the glycerol formal is about 50:50, the phospholipid is present in an amount of about 1 to 4 percent by weight of the pharmaceutical composition, and the pharmaceutically active compound comprises florfenicol or a pharmaceutically acceptable ester thereof in an amount of about 1 percent by weight of the pharmaceutical composition, terbinafine or a pharmaceutically acceptable salt thereof in an amount of about 1 percent by weight of the pharmaceutical composition, and betamethasone or a pharmaceutically acceptable ester thereof in an amount of about 0.1 percent by weight of the pharmaceutical composition.

In one embodiment, the first organic solvent is propylene carbonate, the second organic solvent is glycerol formal, the phospholipid is Phospholipon® 90H, the ratio of the propylene carbonate to the glycerol formal ranges from about 60:40 to 40:60, the phospholipid is present in an amount of about 3 percent by weight of the pharmaceutical composition, and the pharmaceutically active compound comprises florfenicol or a pharmaceutically acceptable ester thereof in an amount of about 1 percent by weight of the pharmaceutical composition, terbinafine or a pharmaceutically acceptable salt thereof in an amount of about 1 percent by weight of the pharmaceutical composition, and betamethasone or a pharmaceutically acceptable ester thereof in an amount of about 0.1 percent by weight of the pharmaceutical composition.

In one embodiment, the first organic solvent is propylene carbonate, the second organic solvent is glycerol formal, the phospholipid is Phospholipon® 90H, the ratio of the propylene carbonate to the glycerol formal is about 50:50, the phospholipid is present in an amount of about 3 percent by weight of the pharmaceutical composition, and the pharmaceutically active compound comprises florfenicol or a pharmaceutically acceptable ester thereof in an amount of about 1 percent by weight of the pharmaceutical composition, terbinafine or a pharmaceutically acceptable salt thereof in an amount of about 1 percent by weight of the pharmaceutical composition, and betamethasone or a pharmaceutically acceptable ester thereof in an amount of about 0.1 percent by weight of the pharmaceutical composition.

In one embodiment, the first organic solvent is propylene carbonate, the second organic solvent is glycerol formal, the phospholipid is Phospholipon® 90H, and the pharmaceutically active compound comprises gentamicin or a pharmaceutically acceptable salt thereof, clotrimazole or a pharmaceutically acceptable salt thereof, and betamethasone or a pharmaceutically acceptable ester thereof.

In one embodiment, the first organic solvent is propylene carbonate, the second organic solvent is glycerol formal, the phospholipid is Phospholipon® 90H, the ratio of the propylene carbonate to the glycerol formal ranges from about 60:40 to 40:60, and the pharmaceutically active compound comprises gentamicin or a pharmaceutically acceptable salt thereof, clotrimazole or a pharmaceutically acceptable salt thereof, and betamethasone or a pharmaceutically acceptable ester thereof.

In one embodiment, the first organic solvent is propylene carbonate, the second organic solvent is glycerol formal, the phospholipid is Phospholipon® 90H, the ratio of the propylene carbonate to the glycerol formal is about 50:50, and the pharmaceutically active compound comprises gentamicin or a pharmaceutically acceptable salt thereof, clotrimazole or a pharmaceutically acceptable salt thereof, and betamethasone or a pharmaceutically acceptable ester thereof.

In one embodiment, the first organic solvent is propylene carbonate, the second organic solvent is glycerol formal, the phospholipid is Phospholipon® 90H, the ratio of the propylene carbonate to the glycerol formal ranges from about 60:40 to 40:60, the phospholipid is present in an amount of about 1 to 4 percent by weight of the pharmaceutical composition, and the pharmaceutically active compound comprises gentamicin or a pharmaceutically acceptable salt thereof, clotrimazole or a pharmaceutically acceptable salt thereof, and betamethasone or a pharmaceutically acceptable ester thereof.

In one embodiment, the first organic solvent is propylene carbonate, the second organic solvent is glycerol formal, the phospholipid is Phospholipon® 90H, the ratio of the propylene carbonate to the glycerol formal is about 50:50, the phospholipid is present in an amount of about 1 to 4 percent by weight of the pharmaceutical composition, and the pharmaceutically active compound comprises gentamicin or a pharmaceutically acceptable salt thereof, clotrimazole or a pharmaceutically acceptable salt thereof, and betamethasone or a pharmaceutically acceptable ester thereof.

In one embodiment, the first organic solvent is propylene carbonate, the second organic solvent is glycerol formal, the phospholipid is Phospholipon® 90H, the ratio of the propylene carbonate to the glycerol formal ranges from about 60:40 to 40:60, the phospholipid is present in an amount of about 3 percent by weight of the pharmaceutical composition, and the pharmaceutically active compound comprises gentamicin or a pharmaceutically acceptable salt thereof, clotrimazole or a pharmaceutically acceptable salt thereof, and betamethasone or a pharmaceutically acceptable ester thereof.

In one embodiment, the first organic solvent is propylene carbonate, the second organic solvent is glycerol formal, the phospholipid is Phospholipon® 90H, the ratio of the propylene carbonate to the glycerol formal is about 50:50, the phospholipid is present in an amount of about 3 percent by weight of the pharmaceutical composition, and the pharmaceutically active compound comprises gentamicin or a pharmaceutically acceptable salt thereof, clotrimazole or a pharmaceutically acceptable salt thereof, and betamethasone or a pharmaceutically acceptable ester thereof.

In one embodiment, the first organic solvent is propylene carbonate, the second organic solvent is glycerol formal, the phospholipid is Phospholipon® 90H, and the pharmaceutically active compound comprises gentamicin or a pharmaceutically acceptable salt thereof in an amount of about 1 to 3 percent by weight of the pharmaceutical composition, clotrimazole or a pharmaceutically acceptable salt thereof in an amount of about 1 to 3 percent by weight of the pharmaceutical composition, and betamethasone or a pharmaceutically acceptable ester thereof in an amount of about 0.05 to 0.3 percent by weight of the pharmaceutical composition.

In one embodiment, the first organic solvent is propylene carbonate, the second organic solvent is glycerol formal, the phospholipid is Phospholipon® 90H, the ratio of the propylene carbonate to the glycerol formal ranges from about 60:40 to 40:60, and the pharmaceutically active compound comprises gentamicin or a pharmaceutically acceptable salt thereof in an amount of about 1 to 3 percent by weight of the pharmaceutical composition, clotrimazole or a pharmaceutically acceptable salt thereof in an amount of about 1 to 3 percent by weight of the pharmaceutical composition, and betamethasone or a pharmaceutically acceptable ester thereof in an amount of about 0.05 to 0.3 percent by weight of the pharmaceutical composition.

In one embodiment, the first organic solvent is propylene carbonate, the second organic solvent is glycerol formal, the phospholipid is Phospholipon® 90H, the ratio of the propylene carbonate to the glycerol formal is about 50:50, and the pharmaceutically active compound comprises gentamicin or a pharmaceutically acceptable salt thereof in an amount of about 1 to 3 percent by weight of the pharmaceutical composition, clotrimazole or a pharmaceutically acceptable salt thereof in an amount of about 1 to 3 percent by weight of the pharmaceutical composition, and betamethasone or a pharmaceutically acceptable ester thereof in an amount of about 0.05 to 0.3 percent by weight of the pharmaceutical composition.

In one embodiment, the first organic solvent is propylene carbonate, the second organic solvent is glycerol formal, the phospholipid is Phospholipon® 90H, the ratio of the propylene carbonate to the glycerol formal ranges from about 60:40 to 40:60, the phospholipid is present in an amount of about 1 to 4 percent by weight of the pharmaceutical composition, and the pharmaceutically active compound comprises gentamicin or a pharmaceutically acceptable salt thereof in an amount of about 1 to 3 percent by weight of the pharmaceutical composition, clotrimazole or a pharmaceutically acceptable salt thereof in an amount of about 1 to 3 percent by weight of the pharmaceutical composition, and betamethasone or a pharmaceutically acceptable ester thereof in an amount of about 0.05 to 0.3 percent by weight of the pharmaceutical composition.

In one embodiment, the first organic solvent is propylene carbonate, the second organic solvent is glycerol formal, the phospholipid is Phospholipon® 90H, the ratio of the propylene carbonate to the glycerol formal is about 50:50, the phospholipid is present in an amount of about 1 to 4 percent by weight of the pharmaceutical composition, and the pharmaceutically active compound comprises gentamicin or a pharmaceutically acceptable salt thereof in an amount of about 1 to 3 percent by weight of the pharmaceutical composition, clotrimazole or a pharmaceutically acceptable salt thereof in an amount of about 1 to 3 percent by weight of the pharmaceutical composition, and betamethasone or a pharmaceutically acceptable ester thereof in an amount of about 0.05 to 0.3 percent by weight of the pharmaceutical composition.

In one embodiment, the first organic solvent is propylene carbonate, the second organic solvent is glycerol formal, the phospholipid is Phospholipon® 90H, the ratio of the propylene carbonate to the glycerol formal ranges from about 60:40 to 40:60, the phospholipid is present in an amount of about 3 percent by weight of the pharmaceutical composition, and the pharmaceutically active compound comprises gentamicin or a pharmaceutically acceptable salt thereof in an amount of about 1 to 3 percent by weight of the pharmaceutical composition, clotrimazole or a pharmaceutically acceptable salt thereof in an amount of about 1 to 3 percent by weight of the pharmaceutical composition, and betamethasone or a pharmaceutically acceptable ester thereof in an amount of about 0.05 to 0.3 percent by weight of the pharmaceutical composition.

In one embodiment, the first organic solvent is propylene carbonate, the second organic solvent is glycerol formal, the phospholipid is Phospholipon® 90H, the ratio of the propylene carbonate to the glycerol formal is about 50:50, the phospholipid is present in an amount of about 3 percent by weight of the pharmaceutical composition, and the pharmaceutically active compound comprises gentamicin or a pharmaceutically acceptable salt thereof in an amount of about 1 to 3 percent by weight of the pharmaceutical composition, clotrimazole or a pharmaceutically acceptable salt thereof in an amount of about 1 to 3 percent by weight of the pharmaceutical composition, and betamethasone or a pharmaceutically acceptable ester thereof in an amount of about 0.05 to 0.3 percent by weight of the pharmaceutical composition.

In one embodiment, the first organic solvent is propylene carbonate, the second organic solvent is glycerol formal, the phospholipid is Phospholipon® 90H, and the pharmaceutically active compound comprises gentamicin or a pharmaceutically acceptable salt thereof in an amount of about 1 percent by weight of the pharmaceutical composition, clotrimazole or a pharmaceutically acceptable salt thereof in an amount of about 1 percent by weight of the pharmaceutical composition, and betamethasone or a pharmaceutically acceptable ester thereof in an amount of about 0.1 percent by weight of the pharmaceutical composition.

In one embodiment, the first organic solvent is propylene carbonate, the second organic solvent is glycerol formal, the phospholipid is Phospholipon® 90H, the ratio of the propylene carbonate to the glycerol formal ranges from about 60:40 to 40:60, and the pharmaceutically active compound comprises gentamicin or a pharmaceutically acceptable salt thereof in an amount of about 1 percent by weight of the pharmaceutical composition, clotrimazole or a pharmaceutically acceptable salt thereof in an amount of about 1 percent by weight of the pharmaceutical composition, and betamethasone or a pharmaceutically acceptable ester thereof in an amount of about 0.1 percent by weight of the pharmaceutical composition.

In one embodiment, the first organic solvent is propylene carbonate, the second organic solvent is glycerol formal, the phospholipid is Phospholipon® 90H, the ratio of the propylene carbonate to the glycerol formal is about 50:50, and the pharmaceutically active compound comprises gentamicin or a pharmaceutically acceptable salt thereof in an amount of about 1 percent by weight of the pharmaceutical composition, clotrimazole or a pharmaceutically acceptable salt thereof in an amount of about 1 percent by weight of the pharmaceutical composition, and betamethasone or a pharmaceutically acceptable ester thereof in an amount of about 0.1 percent by weight of the pharmaceutical composition.

In one embodiment, the first organic solvent is propylene carbonate, the second organic solvent is glycerol formal, the phospholipid is Phospholipon® 90H, the ratio of the propylene carbonate to the glycerol formal ranges from about 60:40 to 40:60, the phospholipid is present in an amount of about 1 to 4 percent by weight of the pharmaceutical composition, and the pharmaceutically active compound comprises gentamicin or a pharmaceutically acceptable salt thereof in an amount of about 1 percent by weight of the pharmaceutical composition, clotrimazole or a pharmaceutically acceptable salt thereof in an amount of about 1 percent by weight of the pharmaceutical composition, and betamethasone or a pharmaceutically acceptable ester thereof in an amount of about 0.1 percent by weight of the pharmaceutical composition.

In one embodiment, the first organic solvent is propylene carbonate, the second organic solvent is glycerol formal, the phospholipid is Phospholipon® 90H, the ratio of the propylene carbonate to the glycerol formal is about 50:50, the phospholipid is present in an amount of about 1 to 4 percent by weight of the pharmaceutical composition, and the pharmaceutically active compound comprises gentamicin or a pharmaceutically acceptable salt thereof in an amount of about 1 percent by weight of the pharmaceutical composition, clotrimazole or a pharmaceutically acceptable salt thereof in an amount of about 1 percent by weight of the pharmaceutical composition, and betamethasone or a pharmaceutically acceptable ester thereof in an amount of about 0.1 percent by weight of the pharmaceutical composition.

In one embodiment, the first organic solvent is propylene carbonate, the second organic solvent is glycerol formal, the phospholipid is Phospholipon® 90H, the ratio of the propylene carbonate to the glycerol formal ranges from about 60:40 to 40:60, the phospholipid is present in an amount of about 3 percent by weight of the pharmaceutical composition, and the pharmaceutically active compound comprises gentamicin or a pharmaceutically acceptable salt thereof in an amount of about 1 percent by weight of the pharmaceutical composition, clotrimazole or a pharmaceutically acceptable salt thereof in an amount of about 1 percent by weight of the pharmaceutical composition, and betamethasone or a pharmaceutically acceptable ester thereof in an amount of about 0.1 percent by weight of the pharmaceutical composition.

In one embodiment, the first organic solvent is propylene carbonate, the second organic solvent is glycerol formal, the phospholipid is Phospholipon® 90H, the ratio of the propylene carbonate to the glycerol formal is about 50:50, the phospholipid is present in an amount of about 3 percent by weight of the pharmaceutical composition, and the pharmaceutically active compound comprises gentamicin or a pharmaceutically acceptable salt thereof in an amount of about 1 percent by weight of the pharmaceutical composition, clotrimazole or a pharmaceutically acceptable salt thereof in an amount of about 1 percent by weight of the pharmaceutical composition, and betamethasone or a pharmaceutically acceptable ester thereof in an amount of about 0.1 percent by weight of the pharmaceutical composition.

In each pharmaceutical composition described in this section, the glycerol formal can be replaced with propylene glycol.

4.5.2 Pharmaceutical Compositions Comprising (i) a Phospholipid or Sphingomyelin, a Solvent of Selected from the Group Consisting of Propylene Glycol Substantially Free of Other Organic Solvents and Glycerol Formal Substantially Free of Other Organic Solvents, and (iii) a Pharmaceutically Active Agent Any pharmaceutically active agent described above that is compatible with the phospholipid and the propylene glycol or glycerol formal can be used in the pharmaceutical compositions.

Any phospholipid or sphingomyelin described above can be used in the pharmaceutical compositions.

4.5.2.1 The Propylene Glycol or Glycerol Formal

Propylene glycol is an organic solvent represented by the formula:

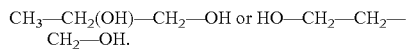

In one embodiment, the proplene glycol is 1,2-propylene glycol. In another embodiment, the propylene glycol is 1,3-propylene glycol. In one embodiment, the proplene glycol is a mixture of 1,2-propylene glycol and 1,3-propylene glycol.

Glycerol formal is an organic solvent of formula $C_4H_8O_3$ and exists as a mixture of 5-hydroxy-1,3-dioxane and 4-hydroxymethyl-1,3-dioxolane in a ratio of about 60:40. Although the solvent glycerol formal consists of two chemical compounds, the two chemical compounds being in a specific ratio of about 60:40, it is typically considered a "solvent" rather than a mixture of compounds. This is because the 5-hydroxy-1,3-dioxane and 4-hydroxymethyl-1,3-dioxolane are in equilibrium with each other. Accordingly, the term glycerol formal (i.e., a mixture of 5-hydroxy-1,3-dioxane and 4-hydroxymethyl-1,3-dioxolane in a ratio of about 60:40), as used herein, is an organic solvent substantially free of other organic solvents.

The propylene glycol and the glycerol formal can include small amounts of impurities. Typically, the propylene glycol and the glycerol formal has a purity of greater than 95 percent by weight, preferably greater than 98 percent by weight, more preferably greater than 99 percent by weight. The solvent, especially glycerol formal, can include a stabilizer. Typically, the stabilizer is present in an amount of 0.5 weight percent or less, preferably an amount of 0.25 weight percent or less, and most preferably an amount of 0.5 weight percent or less. For example, commercially available glycerol formal typical contains ethylenediaminetetraacetate (EDTA), thiodipropionic acid, and propyl gallate as stabilizers.

In one embodiment, the propylene glycol or the glycerol formal is substantially free of water. Propylene glycol or glycerol formal substantially free of water is advantageous since they are not conducive to bacterial growth. Accordingly, it is typically not necessary to include a preservative in pharmaceutical compositions that are substantially free of water. However, in some embodiments, the non-aqueous pharmaceutical composition of the invention can contain a preservative.

The amount of the propylene glycol or the glycerol formal in the pharmaceutical composition typically ranges from about 20 to about 99 percent by weight of the pharmaceutical composition.

In one embodiment, the amount of the propylene glycol or the glycerol formal in the pharmaceutical composition ranges from about 35 to about 90 percent by weight of the pharmaceutical composition.

In one embodiment, the amount of the propylene glycol or the glycerol formal in the pharmaceutical composition is at least about 35 percent by weight of the pharmaceutical composition.

In one embodiment, the amount of the propylene glycol or the glycerol formal in the pharmaceutical composition is at least about 50 percent by weight of the pharmaceutical composition.

In one embodiment, the amount of the propylene glycol or the glycerol formal in the pharmaceutical composition is at least about 75 percent by weight of the pharmaceutical composition.

In one embodiment, the amount of the propylene glycol or the glycerol formal in the pharmaceutical composition is at least about 85 percent by weight of the pharmaceutical composition.

4.5.2.2 Representative Pharmaceutical Formulations

In one embodiment, the solvent is propylene glycol or glycerol formal and the phospholipid is Phospholipon® 90H (commercially available from Phospholipid GmbH of Cologne, Germany).

In one embodiment, the solvent is propylene glycol or glycerol formal, the phospholipid is Phospholipon® 90H, and the phospholipid is present in an amount of about 1 to 4 percent by weight of the pharmaceutical composition.

In one embodiment, the solvent is propylene glycol or glycerol formal, the phospholipid is Phospholipon® 90H, and the phospholipid is present in an amount of about 1 to 2 percent by weight of the pharmaceutical composition.

In one embodiment, the solvent is propylene glycol or glycerol formal, the phospholipid is Phospholipon® 90H, and the pharmaceutically active compound is at least one of an antibacterial agent, an antifungal agent, or a steroid.

In one embodiment, the solvent is propylene glycol or glycerol formal, the phospholipid is Phospholipon® 90H, the phospholipid is present in an amount of about 1 to 4 percent by weight of the pharmaceutical composition, and the pharmaceutically active compound is at least one of an antibacterial agent, an antifungal agent, or a steroid.

In one embodiment, the solvent is propylene glycol or glycerol formal, the phospholipid is Phospholipon® 90H, the phospholipid is present in an amount of about 1 to 2 percent by weight of the pharmaceutical composition, and the pharmaceutically active compound is at least one of an antibacterial agent, an antifungal agent, or a steroid.

In one embodiment, the solvent is propylene glycol or glycerol formal, the phospholipid is Phospholipon® 90H, and the pharmaceutically active compound comprises terbinafine.

In one embodiment, the solvent is propylene glycol or glycerol formal, the phospholipid is Phospholipon® 90H, the phospholipid is present in an amount of about 1 to 4 percent by weight of the pharmaceutical composition, and the pharmaceutically active compound comprises terbinafine.

In one embodiment, the solvent is propylene glycol or glycerol formal, the phospholipid is Phospholipon® 90H, the phospholipid is present in an amount of about 1 to 2 percent by weight of the pharmaceutical composition, and the pharmaceutically active compound comprises terbinafine.

In one embodiment, the solvent is propylene glycol or glycerol formal, the phospholipid is Phospholipon® 90H, and the pharmaceutically active compound comprises gentamicin.

In one embodiment, the solvent is propylene glycol or glycerol formal, the phospholipid is Phospholipon® 90H, the phospholipid is present in an amount of about 1 to 4 percent by weight of the pharmaceutical composition, and the pharmaceutically active compound comprises gentamicin.

In one embodiment, the solvent is propylene glycol or glycerol formal, the phospholipid is Phospholipon® 90H, the phospholipid is present in an amount of about 1 to 2 percent by weight of the pharmaceutical composition, and the pharmaceutically active compound comprises gentamicin.

In one embodiment, the solvent is propylene glycol or glycerol formal, the phospholipid is Phospholipon® 90H, and the pharmaceutically active compound comprises tobramycin.

In one embodiment, the solvent is propylene glycol or glycerol formal, the phospholipid is Phospholipon® 90H, the phospholipid is present in an amount of about 1 to 4 percent by weight of the pharmaceutical composition, and the pharmaceutically active compound comprises tobramycin.

In one embodiment, the solvent is propylene glycol or glycerol formal, the phospholipid is Phospholipon® 90H, the phospholipid is present in an amount of about 1 to 2 percent by weight of the pharmaceutical composition, and the pharmaceutically active compound comprises tobramycin.

In one embodiment, the solvent is propylene glycol or glycerol formal, the phospholipid is Phospholipon® 90H, and the pharmaceutically active compound comprises azithromycin.

In one embodiment, the solvent is propylene glycol or glycerol formal, the phospholipid is Phospholipon® 90H, the phospholipid is present in an amount of about 1 to 4 percent by weight of the pharmaceutical composition, and the pharmaceutically active compound comprises azithromycin.

In one embodiment, the solvent is propylene glycol or glycerol formal, the phospholipid is Phospholipon® 90H, the phospholipid is present in an amount of about 1 to 2 percent by weight of the pharmaceutical composition, and the pharmaceutically active compound comprises azithromycin.

In one embodiment, the solvent is propylene glycol or glycerol formal, the phospholipid is Phospholipon® 90H, and the pharmaceutically active compound comprises florfenicol.

In one embodiment, the solvent is propylene glycol or glycerol formal, the phospholipid is Phospholipon® 90H, the phospholipid is present in an amount of about 1 to 4 percent by weight of the pharmaceutical composition, and the pharmaceutically active compound comprises florfenicol.

In one embodiment, the solvent is propylene glycol or glycerol formal, the phospholipid is Phospholipon® 90H, the phospholipid is present in an amount of about 1 to 2 percent by weight of the pharmaceutical composition, and the pharmaceutically active compound comprises florfenicol.

In one embodiment, the solvent is propylene glycol or glycerol formal, the phospholipid is Phospholipon® 90H, and the pharmaceutically active compound comprises an antibacterial agent, an antifungal agent, and a steroid.

In one embodiment, the solvent is propylene glycol or glycerol formal, the phospholipid is Phospholipon® 90H, the phospholipid is present in an amount of about 1 to 4 percent by weight of the pharmaceutical composition, and the pharmaceutically active compound comprises an antibacterial agent, an antifungal agent, and a steroid.

In one embodiment, the solvent is propylene glycol or glycerol formal, the phospholipid is Phospholipon® 90H, the phospholipid is present in an amount of about 1 to 2 percent by weight of the pharmaceutical composition, and the pharmaceutically active compound comprises an antibacterial agent, an antifungal agent, and a steroid.

In one embodiment, the solvent is propylene glycol or glycerol formal, the phospholipid is Phospholipon® 90H, and the pharmaceutically active compound comprises tobramycin or a pharmaceutically acceptable salt thereof, terbinafine or a pharmaceutically acceptable salt thereof, and betamethasone or a pharmaceutically acceptable ester thereof In one embodiment, the solvent is propylene glycol or glycerol formal, the phospholipid is Phospholipon® 90H, the phospholipid is present in an amount of about 1 to 4 percent by weight of the pharmaceutical composition, and the pharmaceutically active compound comprises tobramycin or a pharmaceutically acceptable salt thereof, terbinafine or a pharmaceutically acceptable salt thereof, and betamethasone or a pharmaceutically acceptable ester thereof.

In one embodiment, the solvent is propylene glycol or glycerol formal, the phospholipid is Phospholipon® 90H, the phospholipid is present in an amount of about 1 to 2 percent by weight of the pharmaceutical composition, and the pharmaceutically active compound comprises tobramycin or a pharmaceutically acceptable salt thereof, terbinafine or a pharmaceutically acceptable salt thereof, and betamethasone or a pharmaceutically acceptable ester thereof.

In one embodiment, the solvent is propylene glycol or glycerol formal, the phospholipid is Phospholipon® 90H, and the pharmaceutically active compound comprises tobramycin or a pharmaceutically acceptable salt thereof in an amount of about 1 to 3 percent by weight of the pharmaceutical composition, terbinafine or a pharmaceutically acceptable salt thereof in an amount of about 1 to 3 percent by weight of the pharmaceutical composition, and betamethasone or a pharmaceutically acceptable ester thereof in an amount of about 0.05 to 0.3 percent by weight of the pharmaceutical composition.

In one embodiment, the solvent is propylene glycol or glycerol formal, the phospholipid is Phospholipon® 90H, the phospholipid is present in an amount of about 1 to 4 percent by weight of the pharmaceutical composition, and the pharmaceutically active compound comprises tobramycin or a pharmaceutically acceptable salt thereof in an amount of about 1 to 3 percent by weight of the pharmaceutical composition, terbinafine or a pharmaceutically acceptable salt thereof in an amount of about 1 to 3 percent by weight of the pharmaceutical composition, and betamethasone or a pharmaceutically acceptable ester thereof in an amount of about 0.05 to 0.3 percent by weight of the pharmaceutical composition.

In one embodiment, the solvent is propylene glycol or glycerol formal, the phospholipid is Phospholipon® 90H, the phospholipid is present in an amount of about 1 to 2 percent by weight of the pharmaceutical composition, and the pharmaceutically active compound comprises tobramycin or a pharmaceutically acceptable salt thereof in an amount of about 1 to 3 percent by weight of the pharmaceutical composition, terbinafine or a pharmaceutically acceptable salt thereof in an amount of about 1 to 3 percent by weight of the pharmaceutical composition, and betamethasone or a pharmaceutically acceptable ester thereof in an amount of about 0.05 to 0.3 percent by weight of the pharmaceutical composition.

In one embodiment, the solvent is propylene glycol or glycerol formal, the phospholipid is Phospholipon® 90H, and the pharmaceutically active compound comprises tobramycin or a pharmaceutically acceptable salt thereof in an amount of about 1 percent by weight of the pharmaceutical composition, terbinafine or a pharmaceutically acceptable salt thereof in an amount of about 1 percent by weight of the pharmaceutical composition, and betamethasone or a pharmaceutically acceptable ester thereof in an amount of about 0.1 percent by weight of the pharmaceutical composition.

In one embodiment, the solvent is propylene glycol or glycerol formal, the phospholipid is Phospholipon® 90H, the phospholipid is present in an amount of about 1 to 4 percent by weight of the pharmaceutical composition, and the pharmaceutically active compound comprises tobramycin or a pharmaceutically acceptable salt thereof in an amount of about 1 percent by weight of the pharmaceutical composition, terbinafine or a pharmaceutically acceptable salt thereof in an amount of about 1 percent by weight of the pharmaceutical composition, and betamethasone or a pharmaceutically acceptable ester thereof in an amount of about 0.1 percent by weight of the pharmaceutical composition.

In one embodiment, the solvent is propylene glycol or glycerol formal, the phospholipid is Phospholipon® 90H, the phospholipid is present in an amount of about 1 to 2 percent by weight of the pharmaceutical composition, and the pharmaceutically active compound comprises tobramycin or a pharmaceutically acceptable salt thereof in an amount of about 1 percent by weight of the pharmaceutical composition, terbinafine or a pharmaceutically acceptable salt thereof in an amount of about 1 percent by weight of the pharmaceutical composition, and betamethasone or a pharmaceutically acceptable ester thereof in an amount of about 0.1 percent by weight of the pharmaceutical composition.

In one embodiment, the solvent is propylene glycol or glycerol formal, the phospholipid is Phospholipon® 90H, and the pharmaceutically active compound comprises azithromycin or a pharmaceutically acceptable salt thereof, terbinafine or a pharmaceutically acceptable salt thereof, and betamethasone or a pharmaceutically acceptable ester thereof.

In one embodiment, the solvent is propylene glycol or glycerol formal, the phospholipid is Phospholipon® 90H, the phospholipid is present in an amount of about 1 to 4 percent by weight of the pharmaceutical composition, and the pharmaceutically active compound comprises azithromycin or a pharmaceutically acceptable salt thereof, terbinafine or a pharmaceutically acceptable salt thereof, and betamethasone or a pharmaceutically acceptable ester thereof.

In one embodiment, the solvent is propylene glycol or glycerol formal, the phospholipid is Phospholipon® 90H, the phospholipid is present in an amount of about 1 to 2 percent by weight of the pharmaceutical composition, and the pharmaceutically active compound comprises azithromycin or a pharmaceutically acceptable salt thereof, terbinafine or a pharmaceutically acceptable salt thereof, and betamethasone or a pharmaceutically acceptable ester thereof.

In one embodiment, the solvent is propylene glycol or glycerol formal, the phospholipid is Phospholipon® 90H, and the pharmaceutically active compound comprises azithromycin or a pharmaceutically acceptable salt thereof in an amount of about 1 to 3 percent by weight of the pharmaceutical composition, terbinafine or a pharmaceutically acceptable salt thereof in an amount of about 1 to 3 percent by weight of the pharmaceutical composition, and betamethasone or a pharmaceutically acceptable ester thereof in an amount of about 0.05 to 0.3 percent by weight of the pharmaceutical composition.

In one embodiment, the solvent is propylene glycol or glycerol formal, the phospholipid is Phospholipon® 90H, the phospholipid is present in an amount of about 1 to 4 percent by weight of the pharmaceutical composition, and the pharmaceutically active compound comprises azithromycin or a pharmaceutically acceptable salt thereof in an amount of about 1 to 3 percent by weight of the pharmaceutical composition, terbinafine or a pharmaceutically acceptable salt thereof in an amount of about 1 to 3 percent by weight of the pharmaceutical composition, and betamethasone or a pharmaceutically acceptable ester thereof in an amount of about 0.05 to 0.3 percent by weight of the pharmaceutical composition.

In one embodiment, the solvent is propylene glycol or glycerol formal, the phospholipid is Phospholipon® 90H, the phospholipid is present in an amount of about 1 to 2 percent by weight of the pharmaceutical composition, and the pharmaceutically active compound comprises azithromycin or a pharmaceutically acceptable salt thereof in an amount of about 1 to 3 percent by weight of the pharmaceutical composition, terbinafine or a pharmaceutically acceptable salt thereof in an amount of about 1 to 3 percent by weight of the pharmaceutical composition, and betamethasone or a pharmaceutically acceptable ester thereof in an amount of about 0.05 to 0.3 percent by weight of the pharmaceutical composition.

In one embodiment, the solvent is propylene glycol or glycerol formal, the phospholipid is Phospholipon® 90H, and the pharmaceutically active compound comprises azithromycin or a pharmaceutically acceptable salt thereof in an amount of about 1 percent by weight of the pharmaceutical composition, terbinafine or a pharmaceutically acceptable salt thereof in an amount of about 1 percent by weight of the pharmaceutical composition, and betamethasone or a pharmaceutically acceptable ester thereof in an amount of about 0.1 percent by weight of the pharmaceutical composition.

In one embodiment, the solvent is propylene glycol or glycerol formal, the phospholipid is Phospholipon® 90H, the phospholipid is present in an amount of about 1 to 4 percent by weight of the pharmaceutical composition, and the pharmaceutically active compound comprises azithromycin or a pharmaceutically acceptable salt thereof in an amount of about 1 percent by weight of the pharmaceutical composition, terbinafine or a pharmaceutically acceptable salt thereof in an amount of about 1 percent by weight of the pharmaceutical composition, and betamethasone or a pharmaceutically acceptable ester thereof in an amount of about 0.1 percent by weight of the pharmaceutical composition.

In one embodiment, the solvent is propylene glycol or glycerol formal, the phospholipid is Phospholipon® 90H, the phospholipid is present in an amount of about 1 to 2 percent by weight of the pharmaceutical composition, and the pharmaceutically active compound comprises azithromycin or a pharmaceutically acceptable salt thereof in an amount of about 1 percent by weight of the pharmaceutical composition, terbinafine or a pharmaceutically acceptable salt thereof in an amount of about 1 percent by weight of the pharmaceutical composition, and betamethasone or a pharmaceutically acceptable ester thereof in an amount of about 0.1 percent by weight of the pharmaceutical composition.

In one embodiment, the solvent is propylene glycol or glycerol formal, the phospholipid is Phospholipon® 90H, and the pharmaceutically active compound comprises florfenicol or a pharmaceutically acceptable ester thereof, terbinafine or a pharmaceutically acceptable salt thereof, and betamethasone or a pharmaceutically acceptable ester thereof.

In one embodiment, the solvent is propylene glycol or glycerol formal, the phospholipid is Phospholipon® 90H, the phospholipid is present in an amount of about 1 to 4 percent by weight of the pharmaceutical composition, and the pharmaceutically active compound comprises florfenicol or a pharmaceutically acceptable ester thereof, terbinafine or a pharmaceutically acceptable salt thereof, and betamethasone or a pharmaceutically acceptable ester thereof.

In one embodiment, the solvent is propylene glycol or glycerol formal, the phospholipid is Phospholipon® 90H, the phospholipid is present in an amount of about 1 to 2 percent by weight of the pharmaceutical composition, and the pharmaceutically active compound comprises florfenicol or a pharmaceutically acceptable ester thereof, terbinafine or a pharmaceutically acceptable salt thereof, and betamethasone or a pharmaceutically acceptable ester thereof.

In one embodiment, the solvent is propylene glycol or glycerol formal, the phospholipid is Phospholipon® 90H, and the pharmaceutically active compound comprises florfenicol or a pharmaceutically acceptable ester thereof in an amount of about 1 to 3 percent by weight of the pharmaceutical composition, terbinafine or a pharmaceutically acceptable salt thereof in an amount of about 1 to 3 percent by weight of the pharmaceutical composition, and betamethasone or a pharmaceutically acceptable ester thereof in an amount of about 0.05 to 0.3 percent by weight of the pharmaceutical composition.

In one embodiment, the solvent is propylene glycol or glycerol formal, the phospholipid is Phospholipon® 90H, the phospholipid is present in an amount of about 1 to 4 percent by weight of the pharmaceutical composition, and the pharmaceutically active compound comprises florfenicol or a pharmaceutically acceptable ester thereof in an amount of about 1 to 3 percent by weight of the pharmaceutical composition, terbinafine or a pharmaceutically acceptable salt thereof in an amount of about 1 to 3 percent by weight of the pharmaceutical composition, and betamethasone or a pharmaceutically acceptable ester thereof in an amount of about 0.05 to 0.3 percent by weight of the pharmaceutical composition.

In one embodiment, the solvent is propylene glycol or glycerol formal, the phospholipid is Phospholipon® 90H, the phospholipid is present in an amount of about 1 to 2 percent by weight of the pharmaceutical composition, and the pharmaceutically active compound comprises florfenicol or a pharmaceutically acceptable ester thereof in an amount of about 1 to 3 percent by weight of the pharmaceutical composition, terbinafine or a pharmaceutically acceptable salt thereof in an amount of about 1 to 3 percent by weight of the pharmaceutical composition, and betamethasone or a pharmaceutically acceptable ester thereof in an amount of about 0.05 to 0.3 percent by weight of the pharmaceutical composition.

In one embodiment, the solvent is propylene glycol or glycerol formal, the phospholipid is Phospholipon® 90H, and the pharmaceutically active compound comprises florfenicol or a pharmaceutically acceptable ester thereof in an amount of about 1 percent by weight of the pharmaceutical composition, terbinafine or a pharmaceutically acceptable salt thereof in an amount of about 1 percent by weight of the pharmaceutical composition, and betamethasone or a pharmaceutically acceptable ester thereof in an amount of about 0.1 percent by weight of the pharmaceutical composition.

In one embodiment, the solvent is propylene glycol or glycerol formal, the phospholipid is Phospholipon® 90H, the phospholipid is present in an amount of about 1 to 4 percent by weight of the pharmaceutical composition, and the pharmaceutically active compound comprises florfenicol or a pharmaceutically acceptable ester thereof in an amount of about 1 percent by weight of the pharmaceutical composition, terbinafine or a pharmaceutically acceptable salt thereof in an amount of about 1 percent by weight of the pharmaceutical composition, and betamethasone or a pharmaceutically acceptable ester thereof in an amount of about 0.1 percent by weight of the pharmaceutical composition.

In one embodiment, the solvent is propylene glycol or glycerol formal, the phospholipid is Phospholipon® 90H, the phospholipid is present in an amount of about 1 to 2 percent by weight of the pharmaceutical composition, and the pharmaceutically active compound comprises florfenicol or a pharmaceutically acceptable ester thereof in an amount of about 1 percent by weight of the pharmaceutical composition, terbinafine or a pharmaceutically acceptable salt thereof in an amount of about 1 percent by weight of the pharmaceutical composition, and betamethasone or a pharmaceutically acceptable ester thereof in an amount of about 0.1 percent by weight of the pharmaceutical composition.

In one embodiment, the solvent is propylene glycol or glycerol formal, the phospholipid is Phospholipon® 90H, and the pharmaceutically active compound comprises gentamicin or a pharmaceutically acceptable salt thereof, clotrimazole or a pharmaceutically acceptable salt thereof, and betamethasone or a pharmaceutically acceptable ester thereof.

In one embodiment, the solvent is propylene glycol or glycerol formal, the phospholipid is Phospholipon® 90H, the phospholipid is present in an amount of about 1 to 4 percent by weight of the pharmaceutical composition, and the pharmaceutically active compound comprises gentamicin or a pharmaceutically acceptable salt thereof, clotrimazole or a pharmaceutically acceptable salt thereof, and betamethasone or a pharmaceutically acceptable ester thereof.

In one embodiment, the solvent is propylene glycol or glycerol formal, the phospholipid is Phospholipon® 90H, the phospholipid is present in an amount of about 1 to 2 percent by weight of the pharmaceutical composition, and the pharmaceutically active compound comprises gentamicin or a pharmaceutically acceptable salt thereof, clotrimazole or a pharmaceutically acceptable salt thereof, and betamethasone or a pharmaceutically acceptable ester thereof.

In one embodiment, the solvent is propylene glycol or glycerol formal, the phospholipid is Phospholipon® 90H, and the pharmaceutically active compound comprises gentamicin or a pharmaceutically acceptable salt thereof in an amount of about 1 to 3 percent by weight of the pharmaceutical composition, clotrimazole or a pharmaceutically acceptable salt thereof in an amount of about 1 to 3 percent by weight of the pharmaceutical composition, and betamethasone or a pharmaceutically acceptable ester thereof in an amount of about 0.05 to 0.3 percent by weight of the pharmaceutical composition.

In one embodiment, the solvent is propylene glycol or glycerol formal, the phospholipid is Phospholipon® 90H, the phospholipid is present in an amount of about 1 to 4 percent by weight of the pharmaceutical composition, and the pharmaceutically active compound comprises gentamicin or a pharmaceutically acceptable salt thereof in an amount of about 1 to 3 percent by weight of the pharmaceutical composition, clotrimazole or a pharmaceutically acceptable salt thereof in an amount of about 1 to 3 percent by weight of the pharmaceutical composition, and betamethasone or a pharmaceutically acceptable ester thereof in an amount of about 0.05 to 0.3 percent by weight of the pharmaceutical composition.

In one embodiment, the solvent is propylene glycol or glycerol formal, the phospholipid is Phospholipon® 90H, the phospholipid is present in an amount of about 1 to 2 percent by weight of the pharmaceutical composition, and the pharmaceutically active compound comprises gentamicin or a pharmaceutically acceptable salt thereof in an amount of about 1 to 3 percent by weight of the pharmaceutical composition, clotrimazole or a pharmaceutically acceptable salt thereof in an amount of about 1 to 3 percent by weight of the pharmaceutical composition, and betamethasone or a pharmaceutically acceptable ester thereof in an amount of about 0.05 to 0.3 percent by weight of the pharmaceutical composition.

In one embodiment, the solvent is propylene glycol or glycerol formal, the phospholipid is Phospholipon® 90H, and the pharmaceutically active compound comprises gentamicin or a pharmaceutically acceptable salt thereof in an amount of about 1 percent by weight of the pharmaceutical composition, clotrimazole or a pharmaceutically acceptable salt thereof in an amount of about 1 percent by weight of the pharmaceutical composition, and betamethasone or a pharmaceutically acceptable ester thereof in an amount of about 0.1 percent by weight of the pharmaceutical composition.

In one embodiment, the solvent is propylene glycol or glycerol formal, the phospholipid is Phospholipon® 90H, the phospholipid is present in an amount of about 1 to 4 percent by weight of the pharmaceutical composition, and the pharmaceutically active compound comprises gentamicin or a pharmaceutically acceptable salt thereof in an amount of about 1 percent by weight of the pharmaceutical composition, clotrimazole or a pharmaceutically acceptable salt thereof in an amount of about 1 percent by weight of the pharmaceutical composition, and betamethasone or a pharmaceutically acceptable ester thereof in an amount of about 0.1 percent by weight of the pharmaceutical composition.

In one embodiment, the solvent is propylene glycol or glycerol formal, the phospholipid is Phospholipon® 90H, the phospholipid is present in an amount of about 1 to 2 percent by weight of the pharmaceutical composition, and the pharmaceutically active compound comprises gentamicin or a pharmaceutically acceptable salt thereof in an amount of about 1 percent by weight of the pharmaceutical composition, clotrimazole or a pharmaceutically acceptable salt thereof in an amount of about 1 percent by weight of the pharmaceutical composition, and betamethasone or a pharmaceutically acceptable ester thereof in an amount of about 0.1 percent by weight of the pharmaceutical composition.

4.5.3 General Features of the Pharmaceutical Compositions

In one embodiment, the pharmaceutical composition has a viscosity of greater than about 1,000 cP at 20° C.

In one embodiment, the pharmaceutical composition has a viscosity of greater than about 2,000 cP at 20° C.

In one embodiment, the pharmaceutical composition has a viscosity of greater than about 5,000 cP at 20° C.

In one embodiment, the pharmaceutical composition has a viscosity of greater than about 10,000 cP at 20° C.

In one embodiment, the pharmaceutical composition has a viscosity of greater than about 15,000 cP at 20° C.

In one embodiment, the pharmaceutical composition has a viscosity of greater than about 20,000 cP at 20° C.

In one embodiment, the pharmaceutical composition has a viscosity of greater than about 25,000 cP at 20° C.

Typically, the pharmaceutical composition has a viscosity of less than about 100,000 cP at 20° C.

In one embodiment, the pharmaceutical composition has a viscosity of less than about 75,000 cP at 20° C.

In one embodiment, the pharmaceutical composition has a viscosity that ranges from about 1,000 cP to 100,000 cP at 20° C.

In one embodiment, the pharmaceutical composition has a viscosity that ranges from about 2,000 cP to 100,000 cP at 20° C.

In one embodiment, the pharmaceutical composition has a viscosity that ranges from about 5,000 cP to 100,000 cP at 20° C.

In one embodiment, the pharmaceutical composition has a viscosity that ranges from about 10,000 cP to 100,000 cP at 20° C.

In one embodiment, the pharmaceutical composition has a viscosity that ranges from about 20,000 cP to 100,000 cP at 20° C.

In one embodiment, the pharmaceutical composition has a viscosity that ranges from about 25,000 cP to 100,000 cP at 20° C.

In one embodiment, the pharmaceutical composition has a viscosity that ranges from about 1,000 cP to 75,000 cP at 20° C.

In one embodiment, the pharmaceutical composition has a viscosity that ranges from about 2,000 cP to 75,000 cP at 20° C.

In one embodiment, the pharmaceutical composition has a viscosity that ranges from about 5,000 cP to 75,000 cP at 20° C.

In one embodiment, the pharmaceutical composition has a viscosity that ranges from about 10,000 cP to 75,000 cP at 20° C.

In one embodiment, the pharmaceutical composition has a viscosity that ranges from about 20,000 cP to 75,000 cP at 20° C.

In one embodiment, the pharmaceutical composition has a viscosity that ranges from about 25,000 cP to 75,000 cP at 20° C.

In one embodiment, the pharmaceutical composition has a viscosity that ranges from about 2,000 cP to 25,000 cP at 20° C.

In one embodiment, the pharmaceutical composition has a viscosity that ranges from about 5,000 cP to 25,000 cP at 20° C.

In one embodiment, the pharmaceutical composition has a viscosity that ranges from about 2,000 cP to 18,000 cP at 20° C.

In one embodiment, the pharmaceutical composition has a viscosity that ranges from about 5,000 cP to 18,000 cP at 20° C.

Viscosity is determined using a Brookfield DV-E viscometer (commercially available from Brookfield of Middleboro, Mass.).

4.5.4 Optional Additives

The present pharmaceutical compositions can optionally comprise a suitable amount of a pharmaceutically acceptable preservative, if desired, so as to provide additional protection against microbial growth.

Examples of preservatives useful in the pharmaceutical compositions of the invention include, but are not limited to, potassium sorbate, methylparaben, propylparaben, benzoic acid and its salts, other esters of parahydroxybenzoic acid such as butylparaben, alcohols such as ethyl or benzyl alcohol, phenolic compounds such as phenol, or quarternary compounds such as benzalkonium chlorides (e.g., benzethonium chloride).

In one embodiment, the pharmaceutical compositions of the invention can optionally contain a suitable amount of a pharmaceutically acceptable polymer. The polymer further increases the viscosity of the pharmaceutical composition. Many of the pharmaceutical compositions of the invention lose their gel properties at temperatures greater than about 40° C. By including a polymer in the pharmaceutical compositions, the pharmaceutical compositions maintain their gel properties at higher temperatures.

Suitable polymers for use in the compositions and methods of the invention include, but are not limited to, hydroxypropylcellulose, hydoxypropylmethylcellulose (HPMC), chitosan, polyacrylic acid, and polymethacrylic acid.

In one embodiment, the polymer is HPMC.

In one embodiment, the polymer is hydroxypropylcellulose,

In one embodiment, the polymer is polyacrylic acid. In one embodiment, the polyacrylic acid is a crosslinked polyacrylic acid such as Carbomer® (commercially available from Carbomer, Inc. of Westborough, Mass.).

In one embodiment, the polymer is polymethacrylic acid.

Typically, the polymer is present in an amount ranging from greater than 0 to 10 percent by weight of the pharmaceutical composition.

In one embodiment, the polymer is present in an amount ranging from about 0.1 to 10 percent by weight of the pharmaceutical composition.

In one embodiment, the polymer is present in an amount ranging from about 1 to 7.5 percent by weight of the pharmaceutical composition.

In one embodiment, the polymer is present in an amount ranging from about 1.5 to 5 percent by weight of the pharmaceutical composition.

In one embodiment, the polymer is present in an amount ranging from about 2 to 4 percent by weight of the pharmaceutical composition.

The components of the pharmaceutical composition (the polymer, the solvents, and the pharmaceutically active agent, as well as any other optional components) are preferably biocompatible and non-toxic and, over time, are simply absorbed and/or metabolized by the body.

In one embodiment, the pharmaceutical compositions of the invention are substantially free of polymers.

In one embodiment, any additional components added to the pharmaceutical compositions of the invention are designated as GRAS by the FDA for use or consumption by animals.

In another embodiment, any additional components added to the pharmaceutical compositions of the invention are designated as GRAS by the FDA for use or consumption by humans.

4.6 Methods of Treating a Condition in an Animal

The pharmaceutical compositions of the invention are useful in human medicine and veterinary medicine.

In one embodiment, the method of treating or preventing a condition in an animal comprises administering to the animal in need thereof a therapeutically effective amount of a pharmaceutically active agent by orally administering a pharmaceutical composition of the invention.

In one embodiment, the method of treating or preventing a condition in an animal comprises administering to the animal in need thereof a therapeutically effective amount of a pharmaceutically active agent by otically applying a pharmaceutical composition of the invention.

In one embodiment, the method of treating or preventing a condition in an animal comprises administering to the animal in need thereof a therapeutically effective amount of a pharmaceutically active agent by ophthalmically applying a pharmaceutical composition of the invention.

In one embodiment, the method of treating or preventing a condition in an animal comprises administering to the animal in need thereof a therapeutically effective amount of a pharmaceutically active agent by topically applying a pharmaceutical composition of the invention.

The pharmaceutical compositions of the invention are viscous compositions. Viscous compositions containing drugs have advantages over less viscous (thinner) liquid formulations for treating or preventing conditions in animals. For example, in topical applications, otic applications, and ophthalmic applications, especially veterinary uses, thinner liquid formulations are easily washed or swept away from a target area of delivery than formulations that are more viscous (thicker). For treating conditions such as microbial infections, particularly in non-human animals, the advantages of thicker pharmaceutical compositions include maintaining the pharmaceutically active agent, like antibiotics, in the target area for longer periods of time.

The pharmaceutical compositions of the invention are particularly useful in veterinary medicine, especially for otic applications. For example, when treating or preventing otic microbial infections in small animals, such as cats and dogs, the pharmaceutical composition is typically administered in an amount of about 0.5 mL per ear. Larger amounts, however, can be administered for larger animals.

The pharmaceutical compositions of the invention are advantageous in veterinary medicine, especially for otic application, compared to commercially available pharmaceutical compositions. For example, when treating or preventing otic microbial infections in animals using commercially available pharmaceutical compositions the animal typically shakes its head and dislodges the composition from the target infected area (and often out of the ear entirely). This occurs readily with commercially available antibiotic compositions since they have lower viscosity. However, the pharmaceutical compositions of the invention, having a higher viscosity, are not as easily dislodged, thus rendering them more effective in delivering the pharmaceutically active agent to the target infected area and remaining present for extended periods at the infected area to provide controlled- or sustained-release of the pharmaceutically active agent.

Advantageously, the pharmaceutical compositions of the invention need to be applied less frequently than commercially available pharmaceutical compositions. Often only two doses or a single dose of the pharmaceutical compositions of the invention are effective at treating or preventing otic microbial infections in animals. In contrast, commercially available pharmaceutical compositions typically require many more doses. For example, OTOMAX® (commercially available from Schering-Plough Animal Health of Union NJ) requires 2 doses per day for 7 days.

Further, the pharmaceutical compositions of the invention are typically more lipophilic than aqueous or semi-aqueous formulations. Without being bound by theory, it is believed that the increased lipophilicity of the pharmaceutical compositions of the invention renders them more effective than aqueous or semi-aqueous formulations, particularly for treating or preventing ear infections in an animal, because the pharmaceutical compositions of the invention are more compatible with the highly lipophilic environment of the animal's ear.

The pharmaceutical compositions of the invention also adhere well to the skin and, accordingly, are useful for topical application.

The pharmaceutical compositions of the invention can also be administered orally. To administer the pharmaceutical compositions orally, the pharmaceutical composition can, for example, be encapsulated in a capsule, such as a hard gelatin capsule or a soft gelatin capsule, and the capsule orally administered to the animal. Suitable capsules for use in the invention are Shionogi Qualicaps (commercially available from and Shionogi & Co., Ltd of Osaka, Japan). Oral dosage forms can be designed to release the pharmaceutically active compound in the stomach immediately or almost immediately or to provide sustained release of the pharmaceutically active compound in the stomach. The oral dosage forms can also be designed to release the pharmaceutically active compound in the intestines immediately or almost immediately or to provide sustained release of the pharmaceutically active compound in the intestines. To delay the release of the pharmaceutically active compound until the dosage form reaches the intestines, the capsule is coated with an enteric coating. Typically, the enteric coating is a pH sensitive polymer such as Eudragit® L-100 (commercially available from DeGussa AG of Frankfurt, Germany). The rate of release of the pharmaceutically active compound is varied by varying the amount of phospholipid or sphingomyelin in the pharmaceutical composition and the presence of polymers in the pharmaceutical composition.

When administered topically, otically, or opthalmically, the pharmaceutical compositions of the invention can provide controlled- or sustained-release of the pharmaceutically active agent in a pharmaceutically effective amount for up to about 15 days and even longer.

In one embodiment, the pharmaceutical compositions according to the invention provide controlled- or sustained-release of the pharmaceutically active agent in a pharmaceutically effective amount for at least about 4 to about 15 days.

In another embodiment, the pharmaceutical compositions according to the invention provide controlled- or sustained-release of the pharmaceutically active agent in a pharmaceutically effective amount for at least about 4 to about 10 days.

In another embodiment, the pharmaceutical compositions according to the invention provide controlled- or sustained-release of the pharmaceutically active agent in a pharmaceutically effective amount for at least about 1 week.

In a preferred embodiment, the pharmaceutical compositions of the invention, by providing controlled- or sustained-release of the pharmaceutically active agent, have reduced toxicity, particularly in small animals such as cats and dogs. Accordingly, the pharmaceutical compositions according to the invention have a better therapeutic profile that conventional immediate release formulations. Methods that involve administering a pharmaceutically active agent to an animal by topically, otically, or ophthalmically applying a pharmaceutical composition of the invention permit pharmaceutically active agents to be administered to animals that could potentially (if administered in presently available dosage forms) result in toxicity and even death of the animal being treated. By advantageously providing controlled- or sustained-release of the pharmaceutically active agents, the pharmaceutical composition of the invention can be administered less frequently and therefore also be easier to use, more convenient, and more cost effective than conventional modes of administering pharmaceutically active agents.

The amount of the pharmaceutically active agent(s) that is(are) effective in treating or preventing a condition, e.g., a bacterial infection, can be determined by standard clinical techniques. In addition, in vitro or in vivo assays can optionally be employed to help identify optimal dosage ranges. The precise dose to be employed will also depend on the route of administration, the seriousness of the condition, and the animal being treated and can be decided according to the judgment of a practitioner and/or each animal's circumstances. Suitable effective dosage amounts, however, can typically range from about 0.1 mg/kg of body weight to about 100 mg/kg of body weight, preferably about 1 mg/kg of body weight to about 50 mg/kg of body weight, more preferably from about 2 mg/kg of body weight to about 30 mg/kg of body weight, for example from about 5 mg/kg of body weight to about 100 mg/kg of body weight. The effective dosage amounts described herein refer to total amounts of all pharmaceutically active agents administered; that is, if more than one pharmaceutically active agent is administered, the effective dosage amounts correspond to the total amount administered.

Typically, pharmaceutical composition is administered from about 1 time each day to about 1 time each week until the condition is abated.

In one embodiment, the pharmaceutical composition is administered once each day until the condition is abated.

In one embodiment, the pharmaceutical composition is administered twice each day until the condition is abated.

In one embodiment, the pharmaceutical composition is administered once each week until the condition is abated.

In one embodiment, the pharmaceutical composition is administered twice each week until the condition is abated.

In one embodiment, the pharmaceutical composition is administered about every 12 hours until the condition is abated.

In one embodiment, the pharmaceutical composition is administered a single time. In many cases the pharmaceutical compositions are effective at treating or preventing a condition in an animal.

In one embodiment, the pharmaceutical composition is administered daily for 1 week.

In one embodiment, the pharmaceutical composition is administered about every 7 days for 4 weeks.

In one embodiment, the pharmaceutical composition is administered about every 7 days for 3 weeks.

In one embodiment, the pharmaceutical composition is administered about every 7 days for 2 weeks.

In one embodiment, the pharmaceutical composition is administered twice about 24 hours apart.

In one embodiment, the pharmaceutical composition is administered twice about 48 hours apart.

In one embodiment, the pharmaceutical composition is administered about every 24 hours for about 4 weeks.

In one embodiment, the pharmaceutical composition is administered about every 12 hours for about 4 weeks.

In one embodiment, the pharmaceutical composition is administered about every 24 hours for about 2 weeks.

In one embodiment, the pharmaceutical composition is administered about every 12 hours for about 2 weeks.

In one embodiment, the pharmaceutical composition is administered about every 24 hours for about 1 week.

In one embodiment, the pharmaceutical composition is administered about every 12 hours for about 1 week.

In another embodiment, an effective dosage amount is administered daily until the condition is abated. The total dose may optionally be divided into daily doses and/or into about 2 to 4 individual doses.

In one embodiment, the condition is a bacterial infection.

Representative bacterial infections that can be treated using the pharmaceutical compositions of the invention include, but are not limited to, bacterial infections caused by bacteria of the genus *Pasteurella, Haemophilus, Fusobacterium, Moraxella, Bacteroides, Aeromonas, Escherichia, Enterobacter, Klebsiella, Salmonella, Shigella, Serratia, Ureaplasma, Chlamydia, Actinobacillus, Streptococcus, Edwardsiella, Staphylococcus, Enterococcus, Bordetella, Proteus, Mycoplasma,* or *Mannheimia.*

Representative bacterial infections that can be treated using the pharmaceutically active agents of the invention include, but are not limited to, bacterial infections caused by *Pasteurella haemolytica, Pasteurella multocida, Pasteurella haemolytica, Haemophilus somnus, Actinobacillus pleuropneumoniae, Actinomyces pyogenes, Pseudomonas aeruginosa, Klebsiella Pneumonia, Escherichia Faecalis, Escherichia Coli, Staphylococcus Aureaus, Streptococcus Pyogenes, Bacillus Subtilis, Streptococcus* spp., *Staphylococcus* spp., *Moraxella* spp., *Salmonella* spp., *Bacteroides* spp., *Peptococcus indolicus, Fusobacterium* spp., *Mycoplasma bovis, Mycoplasma dispar, Ureaplasma* spp., *Chlamydia* spp., *Mycoplasma mycoides, Mycoplasma ovipneumonia, Haemophilus influenzae, Klebsiella salmonella, Shigella, Proteus Enterobacter, Serratia,* and *Bordetella bronchoseptica.*

In one embodiment, the condition is a fungal infection.

In one embodiment, the condition is a yeast infection.

Without being bound by theory, it is believed that the pharmaceutical compositions of the invention wherein the pharmaceutical composition is in the form of a gel containing the pharmaceutically active agent(s) allows for higher loading than can be attained with liposomal formulations (where the maximum loading is believed to be only about 1 percent by weight of the liposome-containing composition). Indeed, pharmaceutical composition containing homogenously distributed pharmaceutically active agents in as much as about 5 percent by weight of the pharmaceutical compositions, and even more, are routinely possible using the compositions of the invention. Indeed, pharmaceutical composition containing homogenously distributed pharmaceutically active agents in as much as about 25 percent by weight of the pharmaceutical compositions are possible. The pharmaceutical compositions of the invention are preferably substantially free of liposomes. In one embodiment, the pharmaceutical compositions of the invention are free of liposomes.

In one embodiment, the animal is a non-human animal.

In another embodiment, the animal is a human.

In another embodiment, the animal is a cat.

In another embodiment, the animal is a dog.

In another embodiment, the animal is a cow.

In another embodiment, the animal is a pig.

In another embodiment, the animal is a sheep.

In another embodiment, the animal is a horse.

4.7 Preparing Pharmaceutical Compositions

The pharmaceutical compositions of the invention comprising (i) a phospholipid or sphingomyelin; (ii) a first organic solvent; (iii) a second organic solvent; and (iv) a pharmaceutically active agent, can be prepared, for example, by simply adding the pharmaceutically active agent(s) to a mixture of the first organic solvent and the second organic solvent ("solvent mixture") (typically about 90% of the amount of the solvent mixture desired in the final pharmaceutical composition) and agitating or stirring the resulting mixture until the pharmaceutically active agent(s) dissolve(s). One or more optional additive(s) can simultaneously and/or sequentially be added and the mixture agitated or stirred until the optional additive(s) dissolve(s). The phospholipid is then added to the mixture, with agitation or stirring, and optionally with heat to provide a phospholipid mixture. Typically the mixture is heated at a temperature of less than 100° C., preferably less than 70° C., more preferably less than about 50° C., and most preferably about 40° C. before the phospholipid is added. Additional solvent mixture is then added to provide the desired concentration of the pharmaceutically active agent(s) in the pharmaceutical composition and the phospholipid mixture is allowed to cool to room temperature to provide the pharmaceutical composition.

Similarly the pharmaceutical compositions of the invention comprising (i) a phospholipid or sphingomyelin, a solvent of selected from the group consisting of propylene glycol substantially free of other organic solvents and glycerol formal substantially free of other organic solvents, and (iii) a pharmaceutically active agent can be prepared, for example, by simply adding the pharmaceutically active agent(s) to the propylene glycol or glycerol formal (typically about 90% of the amount of the solvent desired in the final pharmaceutical composition) and agitating or stirring the resulting mixture, optionally with heat, until the pharmaceutically active agent(s) dissolve(s). One or more optional additive(s) can simultaneously and/or sequentially be added and the mixture agitated or stirred until the optional additive(s) dissolve(s). The phospholipid is then added to the mixture, with agitation or stirring, and optionally with heat to provide a phospholipid mixture. Typically the mixture is heated at a temperature of less than 100° C., preferably less than 70° C., more preferably less than about 50° C., and most preferably about 40° C. before the phospholipid is added. Additional propylene glycol or glycerol formal is then added to provide the desired concentration of the pharmaceutically active agent(s) in the pharmaceutical composition and the phospholipid mixture is allowed to cool to room temperature to provide the pharmaceutical composition.

One skilled in the art, however, will readily recognize that modifications to the above-described methods for preparing the pharmaceutical compositions of the invention are possible, for example the order of adding the components to the solvent(s) can be changed.

4.8 Kits

The invention encompasses kits that can simplify the administration of a pharmaceutically active agent to an animal. A typical kit of the invention comprises a unit dosage form of a pharmaceutical composition according to the invention. In one embodiment, the unit dosage form is a container (such as a vial, a pouch, a tube, a syringe, or the like), which can advantageously be sterile, containing a pharmaceutical composition of the invention. The kit can further comprise a label or printed instructions instructing the use of the pharmaceutically active agent to treat or prevent a condition. In another embodiment, the kit comprises a unit dosage form of a pharmaceutical composition of the invention and a dropper, syringe, or other applicator for administering the pharmaceutical composition. Typically, the components of the kit, for example, the unit dosage form and instructions, are contained within a suitable packaging material.

The following examples are set forth to assist in understanding the invention and should not be construed as specifically limiting the invention described and claimed herein. Such variations of the invention, including the substitution of all equivalents now known or later developed, which would be within the purview of those skilled in the art, and changes in formulation or minor changes in experimental design, are to be considered to fall within the scope of the invention incorporated herein.

5. EXAMPLES

Example 5.1

Phospholipid Pharmaceutical Composition in the Form of a Gel

Tobramycin (2.5 g), terbinafine (2.5 g), decanoic acid (6.34 g), betamethasone acetate (250 mg), and benzethonium chloride (50 mg) were dissolved in 150 mL of stabilized glycerol formal and the resulting mixture heated to about 40° C. with stirring to provide a clear solution. To the resulting solution was added 37.5 mL of stabilized glycerol formal and 62.5 mL of propylene carbonate and the resulting solution heated to about 40° C. with stirring to provide a clear solution. Phospholipon®-90H (2.5 g) (commercially available from Phospholipid GmbH of Cologne, Germany) was added to the 40° C. solution with stirring to provide a clear solution. Hydroxypropylmethylcellulose (5 g) was then added to the 40° C. solution with stirring to provide a clear solution. The solution was allowed to cool to room temperature to provide a gel. The resulting gel contains about 1.25% by weight of Phospholipon®.

The resulting gel contained 1% tobramycin as a decanoic acid salt, 1% terbinafine as a decanoic acid salt, 0.1% betamethasone acetate, and 0.02% benzethonium chloride and had a viscosity of 2,346 cP at 20° C.

Example 5.2

Phospholipid Pharmaceutical Composition in the Form of a Gel

Florfenicol (5 g), betamethasone acetate (500 mg), oleic acid (4.8 g), and benzethonium chloride (100 mg) were dissolved in 250 mL of propylene carbonate and the resulting mixture heated to a temperature of between about 40-45° C. with stirring to provide a clear solution. To the resulting solution was added 284.5 g of stabilized glycerol formal and the resulting solution heated to about 40° C. with stirring to provide a clear solution. Phospholipon®-90H (5 g) (commercially available from Phospholipid GmbH of Cologne, Germany) was then added to the 40° C. solution with stirring to provide a clear solution. The solution was allowed to cool to room temperature overnight to provide a gel. The resulting gel had a viscosity of 52,300 cP at 20° C.

The following day, 150 mL of the gel was warmed to about 40° C. to provide a liquid and hydroxypropylmethylcellulose (4.5 g) was added to the liquid at 40° C. and the resulting mixture allowed to stir at 40° C. for about 15 min. The mixture was then cooled to room temperature to provide a gel. The resulting gel contains about 2% by weight of Phospholipon®.

The resulting gel contained 1% florfenicol, 1% terbinafine as an oleic acid salt, 0.1% betamethasone acetate, and 0.02% benzethonium chloride and had a viscosity of 17,880 cP at 20° C.

Example 5.3

Phospholipid Pharmaceutical Composition in the Form of a Gel

Tobramycin (5 g), terbinafine (5 g), decanoic acid (6.35 g), acetic acid (2.21 g), betamethasone acetate (500 mg), and benzethonium chloride (100 mg) were dissolved in 375 mL of stabilized glycerol formal and 90 mL of propylene carbonate were added to the solution. The resulting mixture was heated to about 40° C. and Phospholipon®-90H (5 g) (commercially available from Phospholipid GmbH of Cologne, Germany) was added with stirring to provide a clear solution. Hydroxypropylmethylcellulose (15 g) was then slowly added to the 40° C. solution with stirring. The solution was stirred for 15 min. and then allowed to cool to room temperature to provide a gel. The resulting gel contains about 2.5% by weight of Phospholipon® and about 3% by weight of hydroxypropylmethylcellulose.

The resulting gel contained 1% tobramycin as a mixture of the decanoic acid salt and acetic acid salt, 1% terbinafine as a mixture of the decanoic acid salt and acetic acid salt, 0.1% betamethasone acetate, and 0.02% benzethonium chloride and had a viscosity of 3,650 cP at 20° C.

Example 5.4

Phospholipid Pharmaceutical Composition in the Form of a Gel

Florfenicol (5 g), betamethasone acetate (500 mg), oleic acid (4.8 g), and benzethonium chloride (100 mg) were dissolved in 250 mL of propylene carbonate and the resulting mixture heated to a temperature of between about 40-45° C. with stirring to provide a clear solution. To the resulting solution was added 284.5 g of stabilized glycerol formal and the resulting solution heated to about 40° C. with stirring to provide a clear solution. Phospholipon®-90H (7.5 g) (commercially available from Phospholipid GmbH of Cologne, Germany) was then added to the 40° C. solution with stirring to provide a clear solution. The solution was allowed to cool to room temperature overnight to provide a gel. The resulting gel contains about 3% by weight of Phospholipon®. The resulting gel contained 1% florfenicol, 1%, 0.1% betamethasone acetate, and 0.02% benzethonium chloride and had a viscosity of 65,300 cP at 20° C.

Example 5.5

Phospholipid Pharmaceutical Composition in the Form of a Gel

Tobramycin (2.5 g), terbinafine (2.5 g), decanoic acid (6.35 g), betamethasone acetate (250 mg), and benzethonium chloride (50 mg) were dissolved in 187.5 mL of stabilized glycerol formal and heated to about 40° C. 45 mL of propylene carbonate was added to the solution and the temperature maintained at about 40° C. Phospholipon®-90H (2.5 g) (commercially available from Phospholipid GmbH of Cologne, Germany) was then added to the resulting solution with stirring to provide a clear solution. Hydroxypropylmethylcellulose (10 g) was then slowly added to the 40° C. solution with stirring. The solution was stirred for 15 min. and then allowed to cool to room temperature to provide a gel. The resulting gel contains about 2.5% by weight of Phospholipon® and about 4% by weight of hydroxypropylmethylcellulose.

The resulting gel contained 1% tobramycin as the decanoic acid salt, 1% terbinafine as a the decanoic acid salt, 0.1% betamethasone acetate, and 0.02% benzethonium chloride and had a viscosity of 17,160 cP at 20° C.

Example 5.6

Phospholipid Pharmaceutical Composition in the Form of a Gel

Florfenicol (10 g), terbinafine (10 g), oleic acid (9.7 g), betamethasone acetate (1 g), and benzethonium chloride (1 g) were dissolved in about 500 mL of glycerol formal and the resulting mixture heated to about 40° C. with stirring to provide a solution. To the resulting 40° C. solution was added Phospholipon®-90H (10 g) (commercially available from Phospholipid GmbH of Cologne, Germany) and hydroxypropylmethylcellulose (30 g) with stirring to provide a solution. The solution was then filled to a volume of 1000 mL (at 40° C.) with glycerol formal. The total amount of glycerol formal was 898.46 g. The solution was allowed to cool to room temperature to provide a gel. The resulting gel contains about 1% by weight of Phospholipon®, about 1% by weight florfenicol, about 1% by weight terbinafine as a oleic acid salt, about 0.1% by weight betamethasone acetate, and about 0.1% by weight benzethonium chloride.

Example 5.7

Phospholipid Pharmaceutical Composition in the Form of a Gel

Tobramycin (5 g), terbinafine (5 g), betamethasone acetate (0.5 g), decanoic acid (6.35 g), acetic acid (2.21 g), and benzethonium chloride (0.5 g) were dissolved in about 300 mL of glycerol formal and the resulting mixture heated to a temperature of about 40° C. with stirring to provide a solution. To the resulting 40° C. solution was added Phospholipon®-90H (10 g) (commercially available from Phospholipid GmbH of Cologne, Germany) and hydroxypropylmethylcellulose (10 g) with stirring to provide a solution. The solution was then filled to a volume of 500 mL (at 40° C.) with glycerol formal. The total amount of glycerol formal was 568.66 g. The solution was allowed to cool to room temperature to provide a gel. The resulting gel contains about 2% by weight of Phospholipon®, about 1% by weight tobramycin as a mixture of the decanoic acid salt and acetic acid salt, about 1% by weight terbinafine as a mixture of the decanoic acid salt and acetic acid salt, about 0.1% betamethasone acetate, and about 0.1% benzethonium chloride.

A similar formulation can be made by replacing the tobramycin with azithromycin (8 g).

Example 5.8

Phospholipid Pharmaceutical Composition in the Form of a Gel

About 300 mL of glycerol formal was heated to about 40° C. and decanoic acid (41.7 g) and tilmicosin (108.2 g, 92.4% purity) was added to the glycerol formal. The resulting mixture was stirred to provide a solution. Phospholipon®-90H (15 g) (commercially available from Phospholipid GmbH of Cologne, Germany) was added with stirring to provide a solution. Hydroxypropylmethylcellulose (12 g) was then slowly added to the 40° C. solution with stirring. Glycerol formal was then added to provide a volume of 500 mL (at 40EC) and the solution allowed to cool to room temperature to provide a gel. The resulting gel contains about 3% by weight of Phospholipon®, about 2.4% by weight of hydroxypropylmethylcellulose, and about 20% by weight of tilmicosin as a decanoic acid salt.

A similar formulation can be made by replacing the tilmicosin with azithromycin (100 g).

Example 5.9

Phospholipid Pharmaceutical Composition in the Form of a Gel

Tobramycin (5 g), terbinafine (5 g), betamethasone acetate (0.5 g), decanoic acid (6.35 g), acetic acid (2.21 g), and benzethonium chloride (0.5 g) were dissolved in about 300 mL of glycerol formal and the resulting mixture heated to a temperature of about 40° C. with stirring to provide a solution. To the resulting 40° C. solution was added Phospholipon®-90H (10 g) (commercially available from Phospholipid GmbH of Cologne, Germany) with stirring to provide a solution. The solution was then filled to a volume of 500 mL (at 40° C.) with glycerol formal. The total amount of glycerol formal was 568.66 g. The solution was allowed to cool to room temperature to provide a gel. The resulting gel contains about 2% by weight of Phospholipon®, about 1% by weight tobramycin as a mixture of the decanoic acid salt and acetic acid salt, about 1% by weight terbinafine as a mixture of the decanoic acid salt and acetic acid salt, about 0.1% betamethasone acetate, and about 0.1% benzethonium chloride. This phospholipid pharmaceutical composition in the form of a gel contains no polymers.

Example 5.10

Phospholipid Pharmaceutical Composition in the Form of a Gel

Tobramycin (5 g), terbinafine (5 g), betamethasone acetate (0.5 g), decanoic acid (6.35 g), acetic acid (2.21 g), and benzethonium chloride (0.5 g) were dissolved in about 300 mL of glycerol formal and the resulting mixture heated to a temperature of about 40° C. with stirring to provide a solution. To the resulting 40° C. solution was added Phospholipon®-90H (10 g) (commercially available from Phospholipid GmbH of Cologne, Germany) with stirring to provide a solution. The solution was then filled to a volume of 500 mL (at 40° C.) with glycerol formal. The solution was allowed to cool to room temperature to provide a gel. The resulting gel contains about 2% by weight of Phospholipon®, about 1% by weight tobramycin as a mixture of the decanoic acid salt and acetic acid salt, about 1% by weight terbinafine as a mixture of the decanoic acid salt and acetic acid salt, about 0.1% betamethasone acetate, and about 0.1% benzethonium chloride.

A similar formulation can be made by replacing the tobramycin with azithromycin (8 g).

Example 5.11

Clinical Study

Several dogs with ear infections were administered the pharmaceutical composition of Example 5.1, 5.2, or 5.3.

The following protocol was followed to evaluate the clinical efficacy of the pharmaceutical compositions of the invention.

Dogs with ear infections were examined by a veterinarian on day 0 and each ear was assigned a clinical score based on the following signs related to otis externa: pain, erythema, exudate, swelling, odor and ulceration. The following scale was used:

| | |
|---|---|
| Pain: | 0 = none |
| | 1 = mild/moderate: painful on palpation |
| | 2 = severe: painful when raise the pinna |
| Erythema | 0 = none |
| | 1 = mild/moderate: barely perceptible to obvious redness visible with otoscope |
| | 2 = severe: beet or cherry red or erythema extends into pinna |
| Exudate | 0 = none |
| | 1 = mild/moderate: small amount visible in ear canal |
| | 2 = severe: extending out of ear canal and may be crusted |
| Swelling | 0 = none |
| | 1 = mild moderate: some oclussion of ear canal |
| | 2 = severe: canal completely occluded |
| Odor | 0 = none |
| | 1 = mild/moderate: malodor evident when oinna raised |
| | 2 = severe: malodor evident without raising oinna to expose ear canal |
| Uceration | 0 = none |
| | 1 = mild/moderate: mild abrasions |
| | 2 = severe: abrasions that may be bleeding |

The score for pain, erythema, exudate, swelling, odor and ulceration was combined to provide total clinical score ranging from 0 to 12 with 12 being the most severe otis externa and 0 being the least severe otis externa.

On day 0 the dog also received a physical exam, an ear swab was obtained to submit for a bacterial and yeast culture, and a second ear swab was obtained to prepare a roll smear to identify bacteria and/or yeast. The dogs ear was also cleaned with a cleansing solution free of antimicrobial and anti-inflammatory activity and excess solution was removed from the ear. 0.5 mL of the pharmaceutical composition of Example 5.1, 5.2, or 5.3 was then administered to each infected ear and the ears massaged to distribute the pharmaceutical composition.

On day 7 ( ) 2 days) a clinical score was again assigned to each ear using the same scale as used on day 0. On day 7 ( ) 2 days) 0.5 mL of the same pharmaceutical composition as was administered on day 0 was again administered to each infected ear and the ears massaged to distribute the pharmaceutical composition.

On day 14 ( ) 2 days) a clinical score was again assigned to each ear using the same scale as used on day 0.

Various breeds of dogs were used in the study of both sexes, various body weights, and physiological states. All dogs were at least 8 weeks old and in general good health. For inclusion in the study the dogs had a minimum total clinical score on day 0 of 6, received no treatment with systemic or otic antimicrobials or anti-inflammatories within the last month, intact tympanic membranes, visualization of bacteria or yeast on the roll smear, and no concurrent Otodectes cynotis infections.

The results of the study are provided below in Table I. Dogs in Group A were treated with the pharmaceutical composition of example 5.1, dogs in Group B were treated with the pharmaceutical composition of example 5.2, and dogs in Group C were treated with the pharmaceutical composition of example 5.3.

TABLE I

| | Score | | | | | |
|---|---|---|---|---|---|---|
| | Day 0 | | Day 7 | | Day 14 | |
| Animal No. | Left Ear | Right Ear | Left Ear | Right Ear | Left Ear | Right Ear |
| Group A[1] | | | | | | |
| 1 | 7 | 7 | 3 | 3 | 1 | 1 |
| 4 | 3 | 6 | 2 | 2 | 0 | 2 |
| 7 | 10 | 0 | 1 | 0 | 0 | 0 |
| 10 | 9 | 9 | 4 | 3 | 2 | 0 |
| 13 | 12 | 12 | 2 | 0 | 1 | 0 |
| 16 | 2 | 9 | 3 | 4 | 0 | 4 |
| 19 | 10 | 6 | 3 | 3 | 1 | 2 |
| 22 | 12 | 12 | 6 | 6 | 5 | 5 |
| 25 | 0 | 12 | 0 | 6 | 4 | 5 |
| 28 | 10 | 9 | 4 | 4 | 2 | 3 |
| Group B[2] | | | | | | |
| 2 | 8 | 8 | 3 | 0 | 0 | 0 |
| 5 | 6 | 8 | 2 | 2 | 2 | 0 |
| 8 | 10 | 0 | 4 | 0 | 6 | 0 |
| 11 | 0 | 12 | 0 | 4 | 0 | 1 |
| 14 | 10 | 10 | 0 | 0 | 0 | 0 |
| 17 | 8 | 7 | 0 | 0 | 0 | 0 |
| 20 | 0 | 10 | 0 | 2 | 0 | 0 |
| 23 | 9 | 4 | 4 | 3 | 2 | 0 |
| 26 | 8 | 7 | 1 | 2 | 1 | 1 |
| 29 | 7 | 0 | 3 | 0 | 1 | 0 |
| Group C[3] | | | | | | |
| 3 | 0 | 8 | 0 | 6 | 0 | 6 |
| 6 | 8 | 8 | 2 | 2 | 1 | 0 |
| 9 | 0 | 8 | 0 | 2 | 0 | 2 |
| 12 | 10 | 10 | 4 | 4 | 2 | 2 |
| 15 | 0 | 10 | 0 | 0 | 0 | 0 |
| 18 | 8 | 8 | 8 | 8 | 8 | 8 |
| 21 | 7 | 6 | 2 | 2 | 0 | 1 |
| 24 | 0 | 12 | 0 | 1 | 0 | 4 |
| 27 | 8 | 8 | 2 | 1 | 2 | 0 |
| 30 | 10 | 8 | 1 | 1 | 1 | 0 |

[1]Dogs in Group A were treated with the pharmaceutical composition of example 5.1.
[2]Dogs in Group B were treated with the pharmaceutical composition of example 5.2.
[3]Dogs in Group C were treated with the pharmaceutical composition of example 5.3.

The data in Table I clearly shows that the pharmaceutical compositions of the invention are effective at treating otic microbial infections in dogs.

Example 5.12

Clinical Study

Several dogs with ear infections were administered the pharmaceutical composition of Example 5.6 or Example 5.7. Dogs treated with the pharmaceutical composition of Example 5.6 were designated as Group A and dogs treated with the pharmaceutical composition of Example 5.7 were designated as Group B.

The same protocol as was used in Example 5.10 was used to evaluate the clinical efficacy of the pharmaceutical compositions of the invention.

Dogs with ear infections were examined by a veterinarian on day 0 and each ear was assigned a clinical score based using the scale described in Example 5.10. The score for pain, erythema, exudate, swelling, odor and ulceration was combined to provide total clinical score ranging from 0 to 12 with 12 being the most severe otis externa and 0 being the least severe otis externa.

On day 0 the dog also received a physical exam, a clinical score was assigned to each ear, an ear swab was obtained to submit for a bacterial and yeast culture (a dacron-tipped swab was inserted into the ear canal and then placed in a Port-A-Cul● transport tube (commercially available from BD (Becton, Dickinson and Company) of Franklin Lakes, N.J.) for shipment to a reference laboratory for culturing, and a second ear swab was obtained to prepare a roll smear to identify bacteria and/or yeast (a Q-tip was inserted into the ear canal and then rolled onto a slide and the slide heat fixed and stained using Diff-Quick (commercially available from IMEB Inc. of Chicago, Ill.). 0.5 mL of the pharmaceutical composition of Example 5.6 or Example 5.7 was then administered to each infected ear using a 1 mL syringe and the ears massaged to distribute the pharmaceutical composition.

On day 7, a clinical score was again assigned to each ear using the same scale as used on day 0 and 0.5 mL of the same pharmaceutical composition as was administered on day 0 was again administered to each infected ear and the ears massaged to distribute the pharmaceutical composition.

On day 14, a clinical score was again assigned to each ear using the same scale as used on day 0.

Various breeds of dogs were used in the study of both sexes, various body weights, and physiological states. All dogs were at least 8 weeks old and in general good health. For inclusion in the study the dogs had a minimum total clinical score on day 0 of 6, received no treatment with systemic or otic antimicrobials or anti-inflammatories within the last month, had intact tympanic membranes, showed visualization of bacteria or yeast on the roll smear, and no concurrent *Otodectes cynotis* infections.

The results of the study are provided below in Table II. Dogs in Group A were treated with the pharmaceutical composition of Example 5.6 and dogs in Group B were treated with the pharmaceutical composition of Example 5.7. A final clinical score of 2 in each ear was considered an effective treatment.

TABLE II

| Animal No. | Day 0 Left Ear | Day 0 Right Ear | Day 7 Left Ear | Day 7 Right Ear | Day 14 Left Ear | Day 14 Right Ear |
|---|---|---|---|---|---|---|
| Group A[1] | | | | | | |
| ROB01 | 8 | 8 | 2 | 2 | 1 | 1 |
| ROB03 | 9 | 9 | 3 | 3 | 0 | 0 |
| ROB05 | 6 | 9 | 0 | 3 | 0 | 0 |
| ROB07 | 6 | 8 | 1 | 2 | 0 | 0 |
| ROB09 | 7 | 8 | 2 | 2 | 0 | 0 |
| ROB011 | 7 | 7 | 0 | 0 | 0 | 0 |
| Group B[2] | | | | | | |
| ROB02 | 9 | 9 | 3 | 3 | 0 | 0 |
| ROB04 | 6 | 6 | 2 | 2 | 0 | 0 |
| ROB06 | 10 | 10 | 3 | 3 | 2 | 0 |
| ROB08 | 8 | 8 | 3 | 3 | 6 | 6 |
| ROB010 | 7 | 7 | 1 | 1 | 0 | 0 |
| ROB012 | 9 | 9 | 3 | 3 | 0 | 0 |

[1]Dogs in Group A were treated with the pharmaceutical composition of Example 5.6.
[2]Dogs in Group B were treated with the pharmaceutical composition of Example 5.7.

The data in Table V clearly shows that the otic microbial infection in each dog of Group A was effectively treated (100%) and that the otic microbial infection in each dog of Group B, except for dog ROB08, was effectively treated (83.3%). Dog ROB08, however, did show improvement. The data in Table V clearly shows that the pharmaceutical compositions of the invention are effective at treating otic microbial infections in dogs.

Example 5.13

Stability of the Pharmaceutical Compositions

Pharmaceutical composition, prepared as described in Example 5.1, 5.2, and 5.3 were incubated at a temperature of about 40° C. or about 70° C. for up to 7 days to monitor the degradation of the pharmaceutically active agents as a function of time and temperature. The concentration of the pharmaceutically active agents was determined at each time point by the following procedure:

200 mg of the pharmaceutical composition is weighed into a 100 mL volumetric flask and the flask is filled to volume with 80:20 hexane:ethanol and shaken for about 1 min. The HMPC precipitates. 2 mL of the resulting solution is then filtered through an Acrodisc 25 mm syringe filter (0.2:m Ultipore nylon membrane) and 10:L of the filtered solution is injected onto a Phenomenex Luna, 5:m, CN 100A, 250 mm×4.6 mm, analytical HPLC column. The HPLC is operated at a flow rate of 1 mL/min.and eluted with 65% hexane and 35% undenatured 200 proof ethanol for 20 min. The HPLC is equipped with a UV detector. Terbinafine and florfenicol are detected at 223 nm and Betamethasone acetate is detected at 240 nm. Terbinafine has a retention time of about 4.0 min., betamethasone acetate has a retention time of about 4.4 min., and florfenicol has a retention time of about 7.1 min.

The results of three such stability tests are provided in Table III-V.

TABLE III

Stability of the Pharmaceutical Composition of Example 5.1

| Day | Terbinafine 40° C. | Terbinafine 70° C. | Tobramycin 40° C. | Tobramycin 70° C. | Betamethasone Acetate 40° C. | Betamethasone Acetate 70° C. |
|---|---|---|---|---|---|---|
| 1 | 101.2 | 98.7 | nd[1] | nd | 85.6 | 81.3 |
| 2 | 101.2 | 98.2 | nd | nd | 84.7 | 80.1 |
| 3 | 101.5 | 96.5 | nd | nd | 81.8 | 81.1 |
| 4 | 101.2 | 97.4 | nd | nd | 80.0 | 79.9 |
| 5 | 97.8 | 94.7 | nd | nd | 80.9 | 79.2 |
| 6 | 98.8 | 94.6 | nd | nd | 80.7 | 79.5 |
| 7 | 99.1 | 92.0 | nd | nd | 80.6 | 79.1 |

[1]nd = not determined

TABLE IV

Stability of the Pharmaceutical Composition of Example 5.2

| Day | Terbinafine 40° C. | Terbinafine 70° C. | Florfenicol 40° C. | Florfenicol 70° C. | Betamethasone Acetate 40° C. | Betamethasone Acetate 70° C. |
|---|---|---|---|---|---|---|
| 1 | 99.0 | 101.1 | 102.7 | 113.0 | 100.9 | 101.0 |
| 2 | 99.2 | 99.3 | 102.4 | 105.1 | 101.1 | 98.3 |
| 3 | 98.9 | 97.2 | 104.9 | 101.1 | 101.9 | 97.6 |
| 4 | 98.6 | 97.9 | 100.6 | 99.0 | 100.2 | 97.1 |
| 5 | 100.8 | 92.9 | 104.4 | 96.7 | 99.5 | 97.1 |
| 6 | 98.7 | 92.6 | 97.4 | 97.5 | 100.3 | 98.4 |
| 7 | 98.5 | 92.8 | 104.3 | 107.2 | 100.1 | 97.0 |

TABLE V

Stability of the Pharmaceutical Composition of Example 5.3

| Day | Terbinafine 40° C. | Terbinafine 70° C. | Tobramycin 40° C. | Tobramycin 70° C. | Betamethasone Acetate 40° C. | Betamethasone Acetate 70° C. |
|---|---|---|---|---|---|---|
| 1 | 99.8 | 98.0 | nd[1] | nd | 101.6 | 89.6 |
| 2 | 99.3 | 99.1 | nd | nd | 99.2 | 88.0 |
| 3 | 99.8 | 99.8 | nd | nd | 101.0 | 88.9 |
| 4 | 98.6 | 97.1 | nd | nd | 101.3 | 87.4 |
| 5 | 98.6 | 96.5 | nd | nd | 96.2 | 87.2 |
| 6 | 98.3 | 96.5 | nd | nd | 93.9 | 86.9 |
| 7 | 98.9 | 96.5 | nd | nd | 92.3 | 87.1 |

[1]nd = not determined

The data in Tables III, IV, and V show that the pharmaceutical composition of Example 5.1, 5.2, and 5.3, respectively, have good stability.

5.14 Phospholipid Pharmaceutical Composition for Oral Administration 300 mL of stabilized glycerol formal and 50 mL of propylene glycol were combined and warmed to 40° C. To the resulting solvent mixture was added 41.7 g of decanoic acid and the mixture with stirring to provide a solution. Tilmicosin (108.2 g, 92.4% pure) was then added to the 40° C. solution with stirring to provide a solution. Phospholipon®-90H (15 g) (commercially available from Phospholipid GmbH of Cologne, Germany) was added to the 40° C. solution with stirring to provide a solution. Hydroxypropylmethylcellulose (12 g) was then added to the 40° C. solution with stirring to provide a solution. The solution was filled to a volume of 500 mL at 40° C. and then allowed to cool to room temperature to provide a gel. The resulting gel contains about 3% by weight of Phospholipon®, 2.4% by weight of hydroxypropylmethylcellulose, and 20% by weight of tilmicosin as a decanoic acid salt.

The resulting gel can then be placed in gelatin capsules to provide a capsule containing tilmicosin as a decanoic acid salt.

5.15 Phospholipid Pharmaceutical Composition for Oral Administration 300 mL of stabilized glycerol formal and 75 mL of propylene carbonate were combined and warmed to 40° C. To the resulting solvent mixture was added 41.7 g of decanoic acid and the mixture with stirring to provide a solution. Tilmicosin (108.2 g, 92.4% pure) was then added to the 40° C. solution with stirring to provide a solution. Phospholipon®-90H (15 g) (commercially available from Phospholipid GmbH of Cologne, Germany) was added to the 40° C. solution with stirring to provide a solution. Hydroxypropylmethylcellulose (12 g) was then added to the 40° C. solution with stirring to provide a solution. The solution was filled to a volume of 500 mL at 40° C. and then allowed to cool to room temperature to provide a gel. The resulting gel contains about 3% by weight of Phospholipon®, 2.4% by weight of hydroxypropylmethylcellulose, and 20% by weight of tilmicosin as a decanoic acid salt.

The resulting gel can then be placed in gelatin capsules to provide a capsule containing tilmicosin as a decanoic acid salt.

5.16 Clinical Study

Tilmicosin was orally administered to a dog using the pharmaceutical composition of Example 5.14. A sufficient amount of the gel of example 5.14 was placed in a gelatin capsule to provide a dose of 20 mg/kg to the dog. The dog was then orally administered the gelatin capsule containing the tilmicosin pharmaceutical composition of Example 5.14. Blood was then withdrawn from the dog at various time intervals and the serum concentration of tlmicosin determined by the following procedure:

(i) A C-18 cartridge (commercially available from Waters Corp. of Milford, Mass.) was connected to a 20 mL syringe and to a single diaphragm vacuum pump (commercially available from Gast Manufacturing Inc. of Benton Harbor, Mich.). The C-18 cartridge was condition by washing with 10 mL of methanol followed by 10 mL of deionized water at a flow rate of less than 5 mL per min;

(ii) 1 mL of serum was poured into the syringe and eluted through the C-18 cartridge;

(iii) The cartridge was washed with 10 mL of 25% aqueous acetonitrile followed by 10 mL of water;

(iv) The cartridge was then dried in a desiccator under high vacuum for 10 min;

(v) The cartridge was then eluted into a 2 mL volumetric flask with 5% acetic acid in methanol and the resulting 2 mL sample stored in the refrigerator overnight; and (vi) The sample was then stirred using a vortex mixer and filtered into an amber high pressure liquid chromatography HPLC vial using a Pall acrodisk syringe filter (commercially available from Pall Corp. of East Hills, N.Y.) to provide a solution for analysis of tilmicosin by HPLC.

HPLC analysis was performed by injecting 100:L of the solution on a 25 cm×4.6 mm phenomenex sphericlone 5:m analytical column equipped with a phenomenex phenyl(phenylpropyl) guard column. The HPLC was operated at a flow rate of 1.5 mL/min and eluted using gradient elution according to the following profile:

| Time | Percent Pump A (Acetonitrile) | Percent Pump B (Water) | Percent Pump C (20 mM aqueous Dibutylamine) |
|---|---|---|---|
| 0.0 | 50 | 50 | 0 |
| 3.0 | 50 | 50 | 0 |
| 4.0 | 15 | 85 | 0 |
| 5.0 | 15 | 0 | 85 |
| 25.0 | 25 | 0 | 75 |
| 25.1 | 50 | 50 | 0 |
| 30.0 | 50 | 50 | 0 | for 30 min. The HPLC was equipped with a UV detector operated at 280 nm. Tilmicosin eluted with a retention time of between 13 and 19 min.

The serum concentration of tilmicosin in the serum as a function of time is provided in Table VI.

TABLE VI

Tilmicosin Concentration in Serum as a Function of Time

| Time (hours) | Tilmicosin Concentration (:g/mL) |
|---|---|
| 6 | 0.3 |
| 12 | 0.23 |
| 24 | 0.18 |
| 48 | 0.1 |

The results show that administering the pharmaceutical composition of provides tilmicosin in the blood of the dog for at least 48 h.

Example 5.17

Phospholipid Composition for Topical Administration

A pharmaceutical composition was prepared in substantially the same manner as the pharmaceutical composition described in Example 5.5 and with the same components, except that the pharmaceutical composition contained 0.1% benzethonium chloride.

Example 5.18

Clinical Study

Several dogs with ear infections were administered the pharmaceutical composition of Example 5.17. The following protocol was followed to evaluate the clinical efficacy of the pharmaceutical composition of Example 5.17.

Dogs with ear infections were examined by a veterinarian on day 0 and each ear was assigned a clinical score using the same scale as was used in Example 5.11. If both ears were infected the right ear was designated as the study ear. On day 0 a roll smear was obtained by inserting a Dacron-tipped swab into the ear canal and then rolling the swab onto a slide followed by heat fixing and staining the slide using DifQuik. On day 0 a culture of the dogs infected ear was obtained by inserting a Dacron tipped swab into the ear canal and then placing the swab in a Port-A-Cul transport tube for shipment to a reference laboratory.

For study inclusion, dogs had to be 8 weeks of age or older, have a minimum clinical score of 6, and have intact tympanic membranes. In addition, the presence of either yeast or bacteria on a roll smear was required. Animals were excluded from study enrollment if the clinical score was less than 6; if they had been treated with systemic or otic antimicrobials or parenteral or topical anti-inflammatories, including short-acting corticosteroids within the last 14 days; if they had been treated with parenteral or topical long-acting corticosteroids within the last 28 days; if they had concurrent *Otodectes cynotis* infections; or if foreign bodies were found in the ear canal.

Dogs were divided into two groups, Group A and Group B. Dogs in Group A were administered a single 0.5 mL dose of the pharmaceutical composition of Example 5.17 in each infected ear on day 0 and dogs in Group B were administered a single 1.0 mL dose of the pharmaceutical composition of Example 5.17 in each infected ear on day 0. The appropriate dose was placed in the ear canal with a 1 cc syringe followed by massaging the ear.

Various breeds of dogs were used in the study. Tables VII-X describe the breed, age, gender, and weight of the animals in the study.

TABLE VII

Study Population by Breed

| Breed | Group A | Group B | Total |
|---|---|---|---|
| Bassett Hound | 0 | 1 | 1 |
| Cocker Spaniel | 1 | 1 | 2 |
| Collie | 0 | 2 | 2 |
| Coonhound (Red Tick) | 1 | 0 | 1 |
| Dachshund | 0 | 1 | 1 |
| Dalmation | 0 | 1 | 1 |
| English Toy Spaniel | 0 | 1 | 1 |
| German Shepherd | 0 | 1 | 1 |
| Labrador Retriever | 1 | 0 | 1 |
| Mixed Breed | 3 | 1 | 4 |
| Shih Tzu | 3 | 0 | 3 |
| Standard Poodle | 1 | 1 | 2 |
| Total | 10 | 10 | 20 |

TABLE VIII

Study Population by Age

| Age | Group A | Group B | Total |
|---|---|---|---|
| <1 year | 3 | 3 | 6 |
| >1 and ≦5 years | 3 | 3 | 6 |
| >5 and ≦10 years | 3 | 3 | 6 |
| >10 years | 1 | 1 | 2 |
| Total | 10 | 10 | 20 |

TABLE IX

Study Population by Gender

| Sex | Group A | Group B | Total |
|---|---|---|---|
| Female | 0 | 2 | 2 |
| Spayed female | 2 | 4 | 6 |
| Male | 3 | 3 | 6 |
| Castrated male | 5 | 1 | 6 |
| Total | 10 | 10 | 20 |

TABLE X

Study Population by Body Weight

| Body Weight | Group A | Group B | Total |
|---|---|---|---|
| ≦10 lbs | 2 | 1 | 3 |
| >10 lbs and ≦25 lbs | 2 | 4 | 6 |
| >25 lbs and ≦50 lbs | 1 | 0 | 1 |
| >50 lbs | 5 | 5 | 10 |
| Total | 10 | 10 | 20 |

On day 7 and day 14 a clinical score was again assigned to the infected ear. The results of the study are provided below in Tables XI.

TABLE XI

Clinical Results

| Dog | Group[a] | Score Day 0 | Score Day 7 | Score Day 14 |
|---|---|---|---|---|
| 1 | A | 7 | 3 | 4 |
| 2 | B | 7 | 2 | 1 |
| 3 | A | 9 | 2 | 3 |
| 4 | B | 7 | 4 | 2 |
| 5 | A | 7 | 1 | 1 |
| 6 | B | 10 | 4 | 1 |
| 7 | A | 12 | No visit | 3 |
| 8 | B | 8 | 2 | 1 |
| 9 | A | 9 | 2 | 0 |
| 10 | B | 9 | 5 | 2 |
| 11 | A | 7 | 0 | 0 |
| 12 | B | 9 | 3 | 0 |
| 13 | A | 7 | 2 | 1 |
| 14 | B | 8 | 2 | 0 |
| 15 | A | 11 | 6 | 2 |
| 16 | B | 9 | 2 | 1 |
| 17 | A | 12 | 7 | 2 |
| 18 | B | 9 | 2 | 1 |
| 19 | A | 10 | 4 | 4 |
| 20 | B | 8 | FTC[b] | FTC[b] |

[a] Dogs in Group A were administered a single dose of 0.5 mL of the pharmaceutical composition of Example 5.17 and the dogs of Group B were administered a single dose of 0.5 mL of the pharmaceutical composition of Example 5.17.
[b] FTC = Failed to complete study.

A final clinical score of 2 or less was considered a treatment success. The results in Table XI show that 60 percent of the dogs in Group A and 100 percent of the dogs in Group B were successfully treated.

Table XII describes the culture results.

TABLE XII

Culture Results

| Dog | Group[a] | Bacteria Day 0 | Yeast Day 0[c,d] | Bacteria Day 14 | Yeast Day 14[c,d] |
|---|---|---|---|---|---|
| 1 | A | Negative | Negative | Negative | Negative |
| 2 | B | Negative | MZ (2) | NA | NA |
| 3 | A | S. intermedius (3) | MZ (4) | S. intermedius (2) | MZ (3) |
| 4 | B | S. intermedius (4) | Negative | NA | NA |
| 5 | A | Negative | MZ (4) | NA | NA |
| 6 | B | S. intermedius (4) | Negative | NA | NA |
| 7 | A | S. intermedius (4) | MZ (3) | Not done | Not done |
| 8 | B | S. intermedius (4) | MZ (3) | NA | NA |
| 9 | A | Negative | Negative | NA | NA |
| 10 | B | Negative | Negative | NA | NA |
| 11 | A | Negative | MZ (4) | NA | NA |
| 12 | B | S. intermedius (2) | MZ (1) | NA | NA |
| 13 | A | Negative | MZ (2) | NA | NA |
| 14 | B | S. intermedius (1) | Negative | NA | NA |
| 15 | A | Negative | MZ (3) | NA | NA |
| 16 | B | S. intermedius (4) | Negative | NA | NA |
| 17 | A | S. intermedius (4) | MZ (4) | NA | NA |
| 18 | B | S. intermedius (4) | MZ (3) | NA | NA |
| 19 | A | S. intermedius (4), β-hemolytic Streptococcus | Negative | Not done | Not done |
| 20 | B | S. intermedius (4) | MZ (4) | FTC[b] | FTC |

[a] Dogs in Group A were administered a single dose of 0.5 mL of the pharmaceutical composition of Example 5.17 and the dogs of Group B were administered a single dose of 0.5 mL of the pharmaceutical composition of Example 5.17.
[b] FTC = Failed to complete study.
[c] MZ denotes *Malasezzia pachydermatis*
*Bold entries indicate treatment failures
[d] Scoring scale: 1 = 1 to 10 colonies; 2 = 11 to 100 colonies; 3 = 101 to 1000 colonies; 4 = >1000 colonies.

The results in Table XI and XII clearly show that the pharmaceutical compositions of the invention are effective at treating otic microbial infections in dogs.

5.19: Clinical Study

A male patient bothered with athletes foot his entire life applied a single dose of the pharmaceutical composition of Example 5.17 to the affected area of the foot. Five days after a single application, the skin area that the pharmaceutical composition was applied to was smooth, gaining its natural color back, and itch free whereas the surrounding area was dry, flaky, irritable, and very itchy. The patient reported that the pharmaceutical composition of Example 5.17 was more effective than commercially available antifungal creams that he had been applying twice daily.

5.20: Phospholipid Composition for Topical Administration

Florfenicol (5 g), terbinafine (5 g), oleic acid (4.85 g), betamethasone acetate (500 mg) and benzthonium chloride (100 mg) were suspended in 250 mL (298.4 g) of propylene carbonate in a clean dry 1 liter glass beaker. The mixture was warmed to between 40-45° C. with stirring to provide a clear solution. To the resulting clear solution, maintained at a temperature between 40-45° C., was added 284.5 g of stabilized glycerol with stirring. To the resulting solution was added 10 g of Phospholipon®-90H with stirring while maintaining the temperature between 40-45° C. to provide a clear solution. The solution was allowed to cool slowly to room temperature to provide a gel.

Example 5.21

Clinical Study

Several dogs with ear infections were administered the pharmaceutical composition of Example 5.20. The following protocol was followed to evaluate the clinical efficacy of the pharmaceutical composition of the invention.

Dogs with ear infections were examined by a veterinarian on day 0 and each ear was assigned a clinical score using the same scale as was used in Examples 5.11 and 5.18. If both ears were infected the right ear was designated as the study ear. On day 0 a roll smear was obtained by inserting a Dacron-tipped swab into the ear canal and then rolling the swab onto a slide followed by heat fixing and staining the slide using DifQuik. On day 0 a culture of the dogs infected ear was obtained by inserting a Dacron tipped swab into the ear canal and then placing the swab in a Port-A-Cul transport tube for shipment to a reference laboratory.

For study inclusion, dogs had to be 8 weeks of age or older, have a minimum clinical score of 6, and have intact tympanic membranes. In addition, the presence of either yeast or bacteria on a roll smear was required. Animals were excluded from study enrollment if the clinical score was less than 6; if they had been treated with systemic or otic antimicrobials or parenteral or topical anti-inflammatories, including short-acting corticosteroids within the last 14 days; if they had been treated with parenteral or topical long-acting corticosteroids within the last 28 days; if they had concurrent *Otodectes cynotis* infections; or if foreign bodies were found in the ear canal.

Dogs were administered a single 1.0 mL dose of the pharmaceutical composition of Example 5.20 in each infected ear on day 0 using a 1 cc syringe followed by massaging the ear. Various breeds of dogs were used in the study. Tables XIII-XVI describe the breed, age, gender, and weight of the animals in the study.

TABLE XIII

Study Population by Breed

| Breed | Number |
|---|---|
| Beagle | 1 |
| Boston Terrier | 1 |
| Brittany Spaniel | 1 |
| Cocker Spaniel | 3 |
| Dalmation | 1 |
| Dandie Dinmont Terrier | 1 |
| Golden Retriever | 1 |
| Labrador Retriever | 2 |
| Mixed | 1 |
| Portugese Water Dog | 1 |
| Sharpei | 3 |
| Shih Tzu | 2 |
| Yorkshire Terrier | 2 |
| Total | 20 |

TABLE XIV

Study Population by Age

| Age | Number |
|---|---|
| <1 year | 3 |
| >1 and ≦5 years | 7 |
| >5 and ≦10 years | 2 |
| >10 years | 8 |
| Total | 20 |

TABLE XV

Study Population by Gender

| Sex | Number |
|---|---|
| Female | 2 |
| Spayed female | 6 |
| Male | 5 |
| Castrated male | 7 |
| Total | 20 |

TABLE XVI

Study Population by Body Weight

| Body Weight | Number |
|---|---|
| ≦10 lbs | 2 |
| >10 lbs and ≦25 lbs | 5 |
| >25 lbs and ≦50 lbs | 8 |
| >50 lbs and ≦75 lbs | 3 |
| ≧75 lbs | 2 |
| Total | 20 |

On day 7 and day 14 a clinical score was again assigned to the infected ear. The results of the study are provided below in Tables XVII.

TABLE XVII

Clinical Results

| Dog | Score Day 0 | Score Day 7 | Score Day 14 |
|---|---|---|---|
| 1 | 6 | 1 | 3 |
| 2 | 7 | 4 | 1 |
| 3 | 6 | 2 | 1 |
| 4 | 8 | 8 | 8 |
| 5 | 11 | 2 | 4 |
| 6 | 6 | 6 | 0 |
| 7 | 10 | 5 | 1 |
| 8 | 10 | 4 | 0 |
| 9 | 9 | 3 | 7 |
| 10 | 10 | 4 | 1 |
| 11 | 6 | 2 | 2 |
| 12 | 10 | 6 | 1 |
| 13 | 6 | 1 | 0 |
| 14 | 9 | 2 | 0 |
| 15 | 10 | 0 | 0 |
| 16 | 10 | 3 | 3 |
| 17 | 9 | 5 | 4 |
| 18 | 12 | 6 | 0 |
| 19 | 6 | 2 | 7 |
| 20 | 6 | 1 | 0 |

A final clinical score of 2 or less was considered a treatment success. The results in Table XVII show that 65 percent of the dogs were successfully treated.

Table XIX describes the culture results.

TABLE XIX

Culture Results

| Dog | Bacteria Day 0 | Yeast Day 0[b, c] | Bacteria Day 14 | Yeast Day 14[b, c] |
|---|---|---|---|---|
| 1 | Negative | MZ (3) | Negative | Negative |
| 2 | *S. intermedius* (4), β-hemolytic *Streptococcus* (4) | MZ (2) | NA | NA |
| 3 | *S. intermedius* (4), β-hemolytic *Streptococcus* (4) | MZ (2) | NA | NA |
| 4 | *P. aeruginosa*(4),*S. intermedius* (3) | Negative | *P. aeruginosa* (4) | Negative |
| 5 | Negative | Negative | Negative | Negative |
| 6 | Negative | Negative | NA | NA |
| 7 | *S. intermedius* (4) | MZ (2) | NA | NA |
| 8 | Negative | Negative | NA | NA |
| 9 | ***S. intermedius* (1) | MZ (1) | Negative | MZ (1)** |
| 0 | *S. intermedius*(2) | MZ (3) | NA | NA |
| 11 | Negative | Negative | NA | NA |
| 12 | *S. intermedius*(2) | Negative | NA | NA |
| 13 | Negative | MZ (2) | NA | NA |
| 14 | Negative | MZ (2) | NA | NA |
| 15 | Negative | MZ (2) | NA | NA |
| 16 | Negative | Negative | Negative | Pending |
| 17 | ***S. intermedius*(4) | Negative | Negative | Pending** |
| 18 | Negative | Negative | NA | NA |
| 19 | *S. intermedius* (4) | Negative | Negative | Pending |
| 20 | Negative | Negative | NA | NA |

[c]MZ denotes *Malasezzia pachydermatis*
[d]Scoring scale: 1 = 1 to 10 colonies; 2 = 11 to 100 colonies; 3 = 101 to 1000 colonies; 4 = >1000 colonies.
*Bold entries indicate treatment failures The results in Table XVII and XIX clearly show that the pharmaceutical compositions of the invention are effective at treating otic microbial infections in dogs.

5.22: Phospholipid Composition for Topical Administration

Florfenicol (10 g), betamethasone acetate (1 g), oleic acid (9.7 g), and benzthonium chloride (1 g) were dissolved in 500 mL of propylene carbonate and the resulting mixture heated, with stirring, to a temperature of between about 40 and 45° C. To the resulting heated solution was added Phospholipon®-90H (10 g) and hydroxypropylmethylcellulose (30 g) and the resulting mixture stirred for about 10 min to provide a clear suspension. Propylene glycol was added to the suspension to provide a volume of about 1 L and stirring was continued to provide a clear solution. The resulting solution was allowed to cool slowly to room temperature to provide a gel.

The present invention is not to be limited in scope by the specific embodiments disclosed in the examples which are intended as illustrations of a few aspects of the invention and any embodiments that are functionally equivalent are within the scope of this invention. Indeed, various modifications of the invention in addition to those shown and described herein will become apparent to those skilled in the art and are intended to fall within the scope of the appended claims.

A number of references have been cited, the entire disclosure of which are incorporated herein by reference.

What is claimed is:

1. A method of treating an otic infection in an animal comprising topically administering to the ear of the animal a pharmaceutical composition comprising:
   (i) a mixture of propylene carbonate and glycerol formal in a ratio ranging from about 90:10 to 10:90 containing hydroxypropylmethylcellulose dissolved therein, wherein the hydroxypropylmethylcellulose is present in an amount ranging from about 0.1 to 10% by weight of the composition;
   (ii) a phospholipid in an amount ranging from about 0.1 to 10 percent by weight of the composition, and
   (iii) an antifungal agent, an antibacterial agent, and an anti-inflammatory agent,
wherein the combination of (i), (ii), and (iii) form a gel and the pharmaceutical composition is substantially free of water.

2. The method of claim 1, wherein the phospholipid is present in an amount ranging from about 1% to 4% by weight of the pharmaceutical composition.

3. The method of claim 2, wherein the phospholipid has the structure:

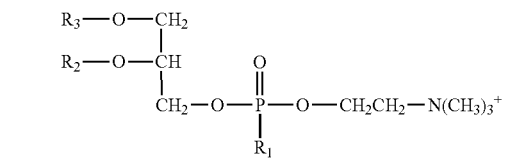

wherein $R_1$ is $-O^{31}$ and $R_2$ and $R_3$ are each independently stearoyl groups or palmitoyl groups wherein the ratio of stearoyl groups to palmitoyl groups is about 85:15.

4. The method of claim 1, wherein the hydroxypropylmethylcellulose is present in an amount ranging from about 2% to 4% by weight of the pharmaceutical composition.

5. The method of claim 1, wherein the phospholipid is present in an amount ranging from about 1% to 4% by weight of the composition and the hydroxypropylmethylcellulose is present in an amount ranging from about 2% to 4% by weight of the pharmaceutical composition.

6. The method of claim 1, wherein the animal is selected from the group consisting of a cat and a dog and the pharmaceutical composition is administered in an amount of about 0.5 mL per ear.

7. A method of treating an otic infection in an animal comprising topically administering to the ear of the animal a pharmaceutical composition comprising:
   (i) a mixture of propylene carbonate and glycerol formal containing hydroxypropylmethylcellulose dissolved therein,
   (ii) a phospholipid, and
   (iii) terbinafine or a pharmaceutically acceptable salt thereof, florfenicol or a pharmaceutically acceptable ester thereof, and betamethasone or a pharmaceutically acceptable ester thereof;
wherein the combination of (i), (ii), and (iii) form a gel and the pharmaceutical composition is substantially free of water.

8. The method of claim 7, wherein the phospholipid is present in an amount ranging from about 1% to 4% by weight of the pharmaceutical composition.

9. The method of claim 8, wherein the phospholipid has the structure:

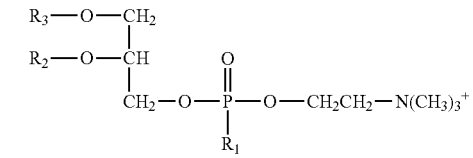

wherein R₁ is —O⁻ and R₂ and R₃ are each independently stearoyl groups or palmitoyl groups wherein the ratio of stearoyl groups to palmitoyl groups is about 85:15.

10. The method of claim 7, wherein the hydroxypropylmethylcellulose is present in an amount ranging from about 2% to 4% by weight of the composition.

11. The method of claim 7, wherein the phospholipid is present in an amount ranging from about 1% to 4% by weight of the composition and the hydroxypropylmethylcellulose is present in an amount ranging from about 2% to 4% by weight of the composition.

12. The method of claim 7, wherein the ratio of propylene carbonate to glycerol formal ranges from about 60:40 to 40:60.

13. The method of claim 7, wherein the terbinafine or a pharmaceutically acceptable salt thereof is present in an amount ranging from about 1% to 3% by weight of the composition, the florfenicol or a pharmaceutically acceptable ester thereof is present in an amount ranging from about 1% to 3% by weight of the composition, and the betamethasone or a pharmaceutically acceptable ester thereof is present in an amount ranging from about 0.05% to 0.3% by weight of the composition.

14. The method of claim 13, wherein the phospholipid is present in an amount ranging from about 1% to 4% by weight of the composition.

15. The method of claim 14, wherein the phospholipid has the structure:

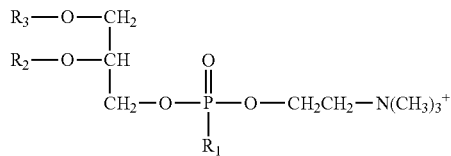

wherein R₁ is —O⁻ and R₂ and R₃ are each independently stearoyl groups or palmitoyl groups wherein the ratio of stearoyl groups to palmitoyl groups is about 85:15.

16. The method of claim 13, wherein the hydroxypropylmethylcellulose is present in an amount ranging from about 2% to 4% by weight of the composition.

17. The method of claim 13, wherein the phospholipid is present in an amount ranging from about 1% to 4% by weight of the composition and the hydroxypropylmethylcellulose is present in an amount ranging from about 2% to 4% by weight of the composition.

18. The method of claim 17, wherein the phospholipid has the structure:

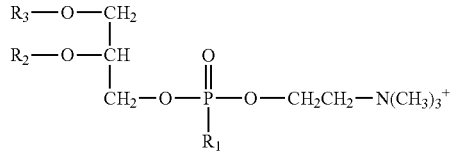

wherein R₁ is —O⁻ and R₂ and R₃ are each independently stearoyl groups or palmitoyl groups wherein the ratio of stearoyl groups to palmitoyl groups is about 85:15.

19. The method of claim 13, wherein the ratio of propylene carbonate to glycerol formal ranges from about 60:40 to 40:60.

20. A method of treating an otic infection in an animal comprising topically administering to the ear of the animal a pharmaceutical composition comprising:
(i) a mixture of propylene carbonate and glycerol formal in a ratio ranging from about 60:40 to 40:60 containing hydroxypropylmethylcellulose dissolved therein;
(ii) a phospholipid having the structure:

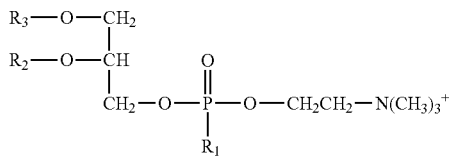

wherein R₁ is —O⁻ and R₂ and R₃ are each independently stearoyl groups or palmitoyl groups wherein the ratio of stearoyl groups to palmitoyl groups is about 85:15;
(iii) terbinafine or a pharmaceutically acceptable salt thereof;
(iv) florfenicol or a pharmaceutically acceptable ester thereof; and
(v) betamethasone or a pharmaceutically acceptable ester thereof, wherein:
the phospholipid is present in an amount ranging from about 1% to 4% by weight of the composition;
the hydroxypropylmethylcellulose is present in an amount ranging from about 2% to 4% by weight of the composition;
the terbinafine or a pharmaceutically acceptable salt thereof is present in an amount ranging from about 1% to 3% by weight of the composition;
the florfenicol or a pharmaceutically acceptable ester thereof is present in an amount ranging from about 1% to 3% by weight of the composition;
the betamethasone or a pharmaceutically acceptable ester thereof is present in an amount ranging from about 0.05% to 0.3% by weight of the composition; and
wherein the combination of (i), (ii), (iii), (iv), and (v) form a gel and the pharmaceutical composition is substantially free of water.

21. A method of treating an otic infection in an animal comprising topically administering to the ear of the animal a pharmaceutical composition comprising:
(i) a mixture of propylene carbonate and glycerol formal in a ratio ranging from about 90:10 to 10:90 containing hydroxypropylmethylcellulose dissolved therein, wherein the hydroxypropylmethylcellulose is present in an amount ranging from about 0.1 to 10% by weight of the composition;
(ii) a phospholipid in an amount ranging from about 0.1 to 10 percent by weight of the composition, and
(iii) an antifungal agent, an antibacterial agent, and an anti-inflammatory agent,
wherein (i), (ii), and (iii) are combined together at a temperature of about 40° C. to provide a solution and then cooled to room temperature provide a gel, and
wherein the pharmaceutical composition is substantially free of water.

22. The method of claim 21, wherein the antifungal agent is terbinafine or a pharmaceutically acceptable salt thereof, the antibacterial agent is florfenicol or a pharmaceutically acceptable ester thereof, and the anti-inflammatory agent is betamethasone or a pharmaceutically acceptable ester thereof.

23. A method of treating an otic infection in an animal comprising topically administering to the ear of the animal a pharmaceutical composition comprising:
(i) a mixture of propylene carbonate and glycerol formal in a ratio ranging from about 60:40 to 40:60 containing hydroxypropylmethylcellulose dissolved therein;
(ii) a phospholipid having the structure:

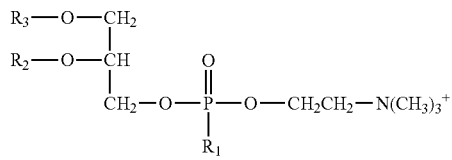

wherein $R_1$ is $-O^-$ and $R_2$ and $R_3$ are each independently stearoyl groups or palmitoyl groups wherein the ratio of stearoyl groups to palmitoyl groups is about 85:15;
(iii) terbinafine or a pharmaceutically acceptable salt thereof;
(iv) florfenicol or a pharmaceutically acceptable ester thereof; and
(v) betamethasone or a pharmaceutically acceptable ester thereof;
wherein:
the phospholipid is present in an amount ranging from about 1% to 4% by weight of the composition;
the hydroxypropylmethylcellulose is present in an amount ranging from about 2% to 4% by weight of the composition;
the terbinafine or a pharmaceutically acceptable salt thereof is present in an amount ranging from about 1% to 3% by weight of the composition;
the florfenicol or a pharmaceutically acceptable ester thereof is present in an amount ranging from about 1% to 3% by weight of the composition;
the betamethasone or a pharmaceutically acceptable ester thereof is present in an amount ranging from about 0.05% to 0.3% by weight of the composition; and
wherein (i), (ii), (iii), (iv), and (v) are combined together at a temperature of about 40° C. to provide a solution and then cooled to room temperature provide a gel, and
wherein the pharmaceutical composition is substantially free of water.

* * * * *